US006635637B2

(12) United States Patent
Wang et al.

(10) Patent No.: US 6,635,637 B2
(45) Date of Patent: Oct. 21, 2003

(54) CYCLIC OXYGUANIDINE PROTEASE INHIBITORS

(75) Inventors: Aihua Wang, Jamison, PA (US); Tianbao Lu, Kennett Square, PA (US); Bruce Edward Tomczuk, Collegeville, PA (US); Richard M. Soll, Lawrenceville, NJ (US); John Curtis Spurlino, Downingtown, PA (US); Roger Francis Bone, Bridgewater, NJ (US)

(73) Assignee: Dimensional Pharmaceuticals, Inc., Exton, PA (US)

( * ) Notice: Subject to any disclaimer, the term of this patent is extended or adjusted under 35 U.S.C. 154(b) by 0 days.

(21) Appl. No.: 09/919,815

(22) Filed: Aug. 2, 2001

(65) Prior Publication Data

US 2002/0022615 A1 Feb. 21, 2002

Related U.S. Application Data

(60) Provisional application No. 60/223,223, filed on Aug. 4, 2000.

(51) Int. Cl.$^7$ .................... C07D 265/02; C07D 273/06; A61K 31/535; A61P 7/02
(52) U.S. Cl. ................. 514/228.8; 514/229.2; 514/231.5; 514/235.5; 514/183; 514/211.08; 514/211.15; 514/364; 514/380; 540/467; 540/544; 540/545; 544/63; 544/66; 544/111; 548/133; 548/240
(58) Field of Search .............. 544/63, 66, 111; 514/228.8, 229.2, 231.5, 235.5

(56) References Cited

U.S. PATENT DOCUMENTS

| | | | |
|---|---|---|---|
| 3,131,218 A | 4/1964 | Spickett et al. | 260/564 |
| 3,271,446 A | 9/1966 | Augstein et al. | 260/564 |
| 3,413,303 A | 11/1968 | Mull | 260/309.6 |
| 4,429,146 A | 1/1984 | Liu | 560/21 |
| 4,499,082 A | 2/1985 | Shenvi et al. | 514/2 |
| 4,727,064 A | 2/1988 | Pitha | 514/58 |
| 4,764,604 A | 8/1988 | Müller | 536/103 |
| 4,764,604 A | 6/1990 | Müller | 536/103 |
| 5,024,998 A | 6/1991 | Bodor | 514/58 |
| 5,466,811 A | 11/1995 | Alexander | 546/283 |
| 5,658,885 A | 8/1997 | Lee et al. | 514/19 |
| 5,792,769 A | 8/1998 | Lu et al. | 514/255 |
| 5,891,909 A | 4/1999 | Soll et al. | 514/517 |
| 6,037,356 A | 3/2000 | Lu et al. | 514/349 |
| 6,326,492 B1 | 12/2001 | Wang et al. | 544/63 |

FOREIGN PATENT DOCUMENTS

| | | |
|---|---|---|
| CA | 2164684 A1 | 6/1996 |
| DE | 1 518 222 | 6/1969 |
| EP | 0 363 284 | 4/1990 |
| EP | 0 604 022 A1 | 6/1994 |
| EP | 0 761 251 A1 | 3/1997 |
| WO | WO 94/20467 | 9/1994 |
| WO | WO 95/07291 | 3/1995 |
| WO | WO 96/11668 | 4/1996 |
| WO | WO 96/18644 | 6/1996 |

(List continued on next page.)

OTHER PUBLICATIONS

Rai et al., PubMed Abstract (Curr Med Chem 8(2):101–19) Feb. 2001.*
Keck, PubMed Abstract (Pancreatology 1(6):656–61), 2001.*
Barton et al., Eight Membered Rings—Mixed Heteroatom Systems, Comprehensive Organic Chemistry, vol. 4, pp. 1166–1170, 1979.*

(List continued on next page.)

Primary Examiner—Deepak Rao
(74) Attorney, Agent, or Firm—Woodcock Washburn LLP

(57) ABSTRACT

Cyclic oxyguanidine compounds, including compounds of Formulae I and II:

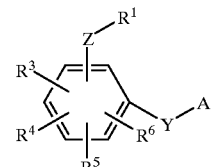

I

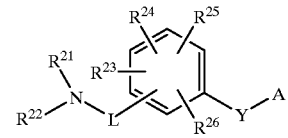

II wherein $R^1$, $R^3$–$R^6$, $R^{21}$–$R^{26}$, L, Y, Z, and A are set forth in the specification, as well as hydrates, solvates or pharmaceutically acceptable salts thereof, that inhibit proteolytic enzymes such as thrombin are described. Also described are methods for preparing the compounds of Formulae I and II. The novel compounds of the present invention are potent inhibitors of proteases, especially trypsin-like serine proteases, such as chymotrypsin, trypsin, thrombin, plasmin and factor Xa. Certain of the compounds exhibit antithrombotic activity via direct, selective inhibition of thrombin, or are intermediates useful for forming compounds having antithrombotic activity. The invention includes a composition for inhibiting loss of blood platelets, inhibiting formation of blood platelet aggregates, inhibiting formation of fibrin, inhibiting thrombus formation, and inhibiting embolus formation in a mammal, comprising a compound of the invention in a pharmaceutically acceptable carrier. Other uses of compounds of the invention are as anticoagulants either embedded in or physically linked to materials used in the manufacture of devices used in blood collection, blood circulation, and blood storage, such as catheters, blood dialysis machines, blood collection syringes and tubes, blood lines and stents.

50 Claims, No Drawings

| | | |
|---|---|---|
| WO | WO 96/32143 | 10/1996 |
| WO | WO 96/38136 | 12/1996 |
| WO | WO 97/01338 | 1/1997 |
| WO | WO 97/11693 | 4/1997 |
| WO | WO 97/22589 | 6/1997 |
| WO | WO 97/24135 | 7/1997 |
| WO | WO 97/30708 | 8/1997 |
| WO | WO 97/36580 | 10/1997 |
| WO | WO 97/46207 | 12/1997 |
| WO | WO 98/16547 | 4/1998 |
| WO | WO 98/23565 | 6/1998 |
| WO | WO 98/31670 | 7/1998 |
| WO | WO 99/26926 | 6/1999 |
| WO | WO 99/51571 | 10/1999 |
| WO | WO 00/73302 A1 | 12/2000 |

OTHER PUBLICATIONS

Augstein, J., et al., "Aryloxyalkylaminoguanidines. Their Synthesis and Biological Properties," *J. Med. Chem.* 10:391–400, American Chemical Society (1967).

Barrett, A.J., "Proteinase inhibitors: potential drugs?" in: *Enzyme Inhibitors as Drugs*, Sandler, M., ed., The MacMillan Press Ltd., London, England, pp. 219–229 (1979).

Baugh, R.J. and Travis, J., "Human Leukocyte Granule Elastase: Rapid Isolation and Characterization," *Biochemistry* 15:836–841, American Chemical Society (1976).

Bodor, N., "Novel Approaches in Prodrug Design," *Drugs of the Future* VI:165–182, J.R. Prous S.A. Publishers (1981).

Brown, F.J., et al., "Design of Orally Active, Non–Peptidic Inhibitors of Human Leukocyte Elastase," *J. Med. Chem.* 37:1259–1261, American Chemical Society (1994).

Bundgaard, H., "Design of prodrugs: Bioreversible derivatives for various functional groups and chemical entities," in: *Design of Prodrugs*, Bundgaard, H., Ed., Elsevier Science Publishers B. V., Amsterdam, The Netherlands, pp. 1–92 (1985).

Claeson, G., "Synthetic peptides and peptidomimetics as substrates and inhibitors of thrombin and other proteases in the blood coagulation system," *Blood Coagulation and Fibrinolysis* 5:411–436, Rapid Communications (1994).

Coughlin, S.R., "Molecular Mechanisms of Thrombin Signaling," *Semin. Hematology* 31:270–277, W.B. Saunders Co. (1994).

Cuypers, H.T., et al., "Sulfhydryl Content of Bovine Eye Lens Leucine Aminopeptidase," *J. Biol. Chem.* 257:7086–7091, American Society of Biological Chemists, Inc. (1982).

Edwards, P.D., et al., "Design, Synthesis, and Kinetic Evaluation of a Unique Class of Elastase Inhibitors, the Peptidyl α–Ketobenzoxazoles, and the X–ray Crystal Structure of the Covalent Complex between Porcine Pancreatic Elastase and Ac–Ala–Pro–Val–2–Benzoxazole," *J. Am. Chem. Soc.* 114:1854–1863, American Chemical Society (1992).

Harker, L.A., "Strategies for inhibiting the effects of thrombin," *Blood Coagulation and Fibrinolysis* 5(*Suppl. 1*):s47–s58, Rapid Communications (1994).

Jeong, J.–H., et al., "Cyclic Guanidino–Sugars with Low $pK_a$ as Transition–State Analog Inhibitors of Glycosidases: Neutral Instead of Charged Species Are The Active Forms," *J. Amer. Chem. Soc.* 118:4227–4234, American Chemical Society (1996).

Khadilkar, B.M. and Samant, S.D., "Synthesis and pharmacology of 2–[3–(4–aryl–1–piperazinyl)–2–hydroxypropyl/ 3–oxopropyl/propoxy]–1H–isoindole–1,3(2H)–diones," *Ind. J. Chem.* 32B:1137–1142, Publications & Information Directorate, CSIR (1993).

Kim, K.S., et al., "Preparation of Argatroban Analog Thrombin Inhibitors with Reduced Basic Guanidine Moiety, And Studies of Their Cell Permeability and Antithrombotic Activities," *Med. Chem. Res.* 6:377–383, Birkhäuser Boston, Inc. (1996).

Kimball, S.D., "Challenges in the development of orally bioavailable thrombin active site inhibitors," *Blood Coagulation and Fibrinolysis* 6:511–519, Rapid Science Publishers (1995).

Lee, S.–L., et al., "Amidino and Guanidino substituted boronic acid inhibitors of trypsin–like enzymes," *CAPLUS Accession No. 1997:594514*, Abstract of U.S. patent 5,658,885 (1997).

Lefkovits, J. and Topol, E.J., "Direct Thrombin Inhibitors in Cardiovascular Medicine," *Circulation* 90:1522–1536, American Heart Association, Inc. (1994).

Mack, H., et al., "Design, Synthesis, and Biological Activity of Novel Rigid Amidino–Phenylalanine Derivatives as Inhibitors of Thrombin," *J. Enzyme Inhib.* 9:73–86, Harwood Academic Publishers GmbH (1995).

Notari, R.E., "Theory and Practice of Prodrug Kinetics," *Meth. Enzym.* 112:309–323, Academic Press, Inc. (1985).

Ozawa, H., et al., "Pharmacological Studies Aminoguanidines. I. Hypotensive and Some General Pharmacological Actions of Benzyl– and Benzylidene–hydrazino–3, 4,5,6–tetrahydropyrimidines," *Yakugaku Zasshi* 95:966–974, Pharmaceutical Society of Japan (1975).

Ripka, W.C. and Vlasuk, G.P., "Chapter 8. Antithrombotics/ Serine Proteases," In: *Annual Reports in Medicinal Chemistry–32*, Bristol, J.A., Ed., Academic Press, Inc., New York, NY, pp. 71–89 (1997).

Saulnier, M.G. et al., "An Efficient Method for the Synthesis of Guanidino Prodrugs," *Bioorg. & Med. Chem. Lett.* 4:1985–1990, Pergamon Press (1994).

Tapparelli, C., et al., "Synthetic low–molecular weight thrombin inhibitors: molecular design and pharmacological profile," *Trends Pharmacol. Sci.* 14:366–376, Elsevier Science Publishers Ltd. (1993).

English language abstract of WO 96/32143 (Document AO2), Derwent World Patents Index, WPI Accession No. 96–476853/199647, 1996.

Dialog File 351, Accession No. 518509, Derwent WPI English language abstract of DE 1 518 222 (Document AL1), 1969.

* cited by examiner

CYCLIC OXYGUANIDINE PROTEASE INHIBITORS

CROSS-REFERENCE TO RELATED APPLICATIONS

This application claims the benefit, under 35 U.S.C. §119(e), of the earlier filing date of U.S. Provisional Application No. 60/223,223, filed on Aug. 4, 2000, which is fully incorporated by reference herein.

BACKGROUND OF THE INVENTION

1. Field of the Invention

The present invention relates to novel compounds that function as enzyme inhibitors, and particularly to a new class of non-peptidic inhibitors of proteolytic enzymes.

2. Background Art

Proteases are enzymes that cleave proteins at single, specific peptide bonds. Proteases can be classified into four generic classes: serine, thiol or cysteinyl, acid or aspartyl, and metalloproteases (Cuypers et al., *J. Biol. Chem.* 257:7086 (1982)). Proteases are essential to a variety of biological activities, such as digestion, formation and dissolution of blood clots, reproduction and the immune reaction to foreign cells and organisms. Aberrant proteolysis is associated with a number of disease states in man and other mammals. The human neutrophil proteases, elastase and cathepsin G, have been implicated as contributing to disease states marked by tissue destruction. These disease states include emphysema, rheumatoid arthritis, corneal ulcers and glomerular nephritis. (Barret, in *Enzyme Inhibitors as Drugs,* Sandler, ed., University Park Press, Baltimore, (1980)). Additional proteases such as plasmin, C-1 esterase, C-3 convertase, urokinase, plasminogen activator, acrosin, and kallikreins play key roles in normal biological functions of mammals. In many instances, it is beneficial to disrupt the function of one or more proteolytic enzymes in the course of therapeutically treating a mammal.

Serine proteases include such enzymes as elastase (human leukocyte), cathepsin G, plasmin, C-1 esterase, C-3 convertase, urokinase, plasminogen activator, acrosin, chymotrypsin, trypsin, thrombin, factor Xa and kallikreins.

Human leukocyte elastase is released by polymorphonuclear leukocytes at sites of inflammation and thus is a contributing cause for a number of disease states. Cathepsin G is another human neutrophil serine protease. Compounds with the ability to inhibit the activity of these enzymes are expected to have an anti-inflammatory effect useful in the treatment of gout, rheumatoid arthritis and other inflammatory diseases, and in the treatment of emphysema. Chymotrypsin and trypsin are digestive enzymes. Inhibitors of these enzymes are useful in treating pancreatitis. Inhibitors of urokinase and plasminogen activator are useful in treating excessive cell growth disease states, such as benign prostatic hypertrophy, prostatic carcinoma and psoriasis.

The serine protease thrombin occupies a central role in hemostasis and thrombosis, and as a multifactorial protein, induces a number of effects on platelets, endothelial cells, smooth muscle cells, leukocytes, the heart, and neurons (Tapparelli et al., *Trends in Pharmacological Sciences* 14:366–376 (1993); Lefkovits and Topol, *Circulation* 90(3): 1522–1536(1994); Harker, *Blood Coagulation and Fibrinolysis* 5 (Suppl 1):S47–S58 (1994)). Activation of the coagulation cascade through either the intrinsic pathway (contact activation) or the extrinsic pathway (activation by exposure of plasma to a non-endothelial surface, damage to vessel walls or tissue factor release) leads to a series of biochemical events that converge on thrombin. Thrombin cleaves fibrinogen ultimately leading to a hemostatic plug (clot formation), potently activates platelets through a unique proteolytic cleavage of the cell surface thrombin receptor (Coughlin, *Seminars in Hematology* 31(4):270–277 (1994)), and auto-amplifies its own production through a feedback mechanism. Thus, inhibitors of thrombin function have therapeutic potential in a host of cardiovascular and non-cardiovascular diseases, including: myocardial infarction; unstable angina; stroke; restenosis; deep vein thrombosis; disseminated intravascular coagulation caused by trauma, sepsis or tumor metastasis; hemodialysis; cardiopulmonary bypass surgery; adult respiratory distress syndrome; endotoxic shock; rheumatoid arthritis; ulcerative colitis; induration; metastasis; hypercoagulability during chemotherapy; Alzheimer's disease; Down's syndrome; fibrin formation in the eye; and wound healing. Other uses include the use of said thrombin inhibitors as anticoagulants either embedded in or physically linked to materials used in the manufacture of devices used in blood collection, blood circulation, and blood storage, such as catheters, blood dialysis machines, blood collection syringes and tubes, blood lines and stents.

Factor Xa is another serine protease in the coagulation pathway. Factor Xa associates with factor Va and calcium on a phospholipid membrane thereby forming aprothrombinase complex. This prothrombinase complex then converts prothrombin to thrombin (Claeson, *Blood Coagulation and Fibrinolysis* 5:411–436 (1994); Harker, *Blood Coagulation and Fibrinolysis* 5 (Suppl 1):S47–S58 (1994)). Inhibitors of factor Xa are thought to offer an advantage over agents that directly inhibit thrombin since direct thrombin inhibitors still permit significant new thrombin generation (Lefkovits and Topol, *Circulation* 90(3):1522–1536 (1994); Harker, *Blood Coagulation and Fibrinolysis* 5 (Suppl 1):S47–S58 (1994)).

A need continues to exist for non-peptidic compounds that are potent and selective protease inhibitors, and which possess greater bioavailability and fewer side-effects than currently available protease inhibitors. Accordingly, new classes of potent protease inhibitors, characterized by potent inhibitory capacity and low mammalian toxicity, are potentially valuable therapeutic agents for a variety of conditions, including treatment of a number of mammalian proteolytic disease states.

BRIEF SUMMARY OF THE INVENTION

The present invention is directed to novel cyclic oxyguanidine compounds having Formulae I and II (below). Also provided are processes for preparing compounds of Formulae I and II, and pharmaceutical compositions comprising a compound of Formula I or II and one or more pharmaceutically acceptable carriers or diluents. The novel compounds of the present invention are potent inhibitors of proteases, especially trypsin-like serine proteases, such as chymotrypsin, trypsin, thrombin, plasmin and factor Xa. Certain of the compounds exhibit antithrombotic activity via direct, selective inhibition of thrombin, or are intermediates useful for forming compounds having antithrombotic activity.

The invention includes a composition for inhibiting loss of blood platelets, inhibiting formation of blood platelet aggregates, inhibiting formation of fibrin, inhibiting thrombus formation, and inhibiting embolus formation in a mammal, comprising a compound of the invention in a pharmaceutically acceptable carrier. These compositions may optionally include anticoagulants, antiplatelet agents, and thrombolytic agents. The compositions can be added to blood, blood products, or mammalian organs in order to effect the desired inhibitions.

Also provided are methods of inhibiting or treating aberrant proteolysis in a mammal, and methods for treating myocardial infarction; unstable angina; stroke; restenosis; deep vein thrombosis; disseminated intravascular coagulation caused by trauma, sepsis or tumor metastasis; hemodialysis; cardiopulmonary bypass surgery; adult respiratory distress syndrome; endotoxic shock; rheumatoid arthritis; ulcerative colitis; induration; metastasis; hypercoagulability during chemotherapy; Alzheimer's disease; Down's syndrome; fibrin formation in the eye; and wound healing. Other uses of compounds of the invention are as anticoagulants either embedded in or physically linked to materials used in the manufacture of devices used in blood collection, blood circulation, and blood storage, such as catheters, blood dialysis machines, blood collection syringes and tubes, blood lines and stents.

The invention also includes a method for reducing the thrombogenicity of a surface in a mammal by attaching to the surface, either covalently or noncovalently, a compound of the invention.

In another aspect, the present invention includes processes for preparing an oxyguanidine compound of the invention.

DETAILED DESCRIPTION OF THE INVENTION

Compounds of the present invention include compounds of Formula I:

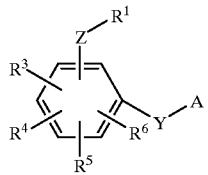

I or a solvate, hydrate or pharmaceutically acceptable salt thereof; wherein:

A is one of

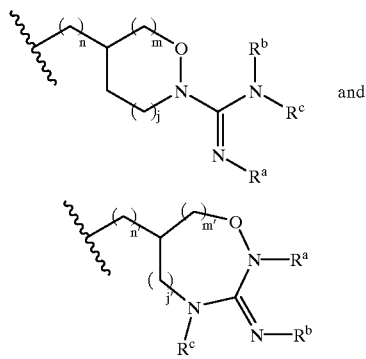

and

Thus, the compounds of Formula I can be represented by Formulae Ia or Ib:

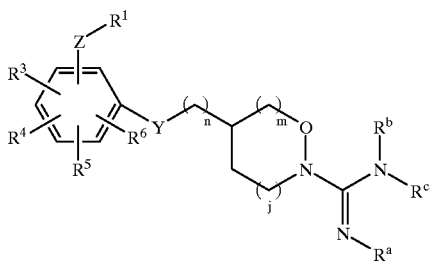

Ia

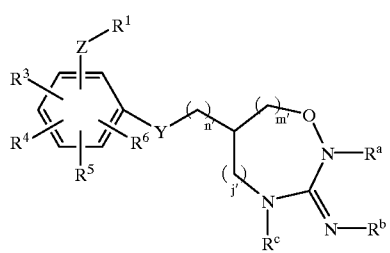

Ib or a solvate, hydrate or pharmaceutically acceptable salt thereof.

For each of Formulae I, Ia and Ib, the following values apply:

$R^1$ is one of alkyl, cycloalkyl, alkenyl, alkynyl, aryl, aralkyl or heteroaryl, any of which may be optionally substituted;

Z is one of —$OSO_2$—, —$SO_2O$—, —$OC(R^yR^z)$—, or —$C(R^yR^z)O$—;

$R^y$ and $R^z$ are each independently one of hydrogen, alkyl, cycloalkyl, aryl, aralkyl, hydroxyalkyl, carboxyalkyl, aminoalkyl, monoalkylaminoalkyl, dialkylaminoalkyl or carboxy;

$R^3$, $R^4$, $R^5$ and $R^6$ are each independently one of hydrogen, alkyl, cycloalkyl, alkenyl, alkynyl, optionally substituted aryl, optionally substituted aralkyl, optionally substituted heteroaryl, trifluoromethyl, halogen, hydroxyalkyl, cyano, nitro, carboxamido, —$CO_2R^x$, —$CH_2OR^x$ or —$OR^x$, or when present on adjacent carbon atoms, $R^4$ and $R^3$ may also be taken together to form one of —CH=CH—CH=CH— or —$(CH_2)_q$—, where q is from 2 to 6, and $R^5$ and $R^6$ are defined as above;

$R^x$, in each instance, is independently one of hydrogen, alkyl or cycloalkyl wherein said alkyl or cycloalkyl groups may optionally have one or more unsaturations;

Y is one of —O—, —$NR^{10}$—, —S—, —$CHR^{10}$— or a covalent bond; and $R^{10}$, in each instance, is independently one of hydrogen, alkyl, aralkyl, aryl, hydroxy($C_{2-10}$)alkyl, amino($C_{2-10}$) alkyl, monoalkylamino($C_{2-10}$)alkyl, dialkylamino ($C_{2-10}$)alkyl or carboxyalkyl;

$R^a$, $R^b$ and $R^c$ are independently hydrogen, alkyl, hydroxy, alkoxy, aryloxy, aralkoxy, alkoxycarbonyloxy, cyano or —$CO_2R^w$, where $R^w$ is alkyl, cycloalkyl, phenyl, benzyl,

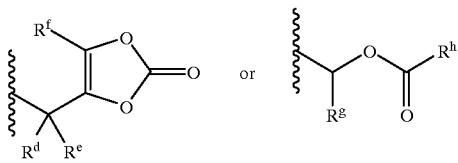

where $R^d$ and $R^e$ are independently hydrogen, $C_{1-6}$ alkyl, $C_{2-6}$ alkenyl or phenyl, $R^f$ is hydrogen, $C_{1-6}$ alkyl, $C_{2-6}$ alkenyl or phenyl, $R^g$ is hydrogen, $C_{1-6}$ alkyl, $C_{2-6}$ alkenyl or phenyl, and $R^h$ is aralkyl or $C_{1-6}$ alkyl;

n and n' are each from zero to 4, preferably zero to 2;
m and m' are each from zero to 4, preferably zero to 2; and
j and j' are each from zero to 4, preferably zero to 2;
provided that n, n', m, m', j and j' are not all zero.

A preferred group of compounds falling within the scope of the present invention include compounds of Formulae Ia and Ib wherein:

$R^1$ is one of $C_{6-10}$ aryl, pyridinyl, thiophenyl (i.e., thiophene), quinazolinyl, quinolinyl or tetrahydroquinolinyl, any of which is optionally substituted by one or two of hydroxy, nitro, trifluoromethyl, halogen, $C_{1-6}$ alkyl, $C_{6-10}$ aryl, $C_{1-6}$ alkoxy, $C_{6-10}$ ar($C_{1-6}$)alkoxy, $C_{1-6}$ aminoalkyl, $C_{1-6}$ aminoalkoxy, amino, mono($C_{1-4}$)alkylamino, di($C_{1-4}$) alkylamino, $C_{2-6}$ alkoxycarbonylamino, $C_{2-6}$ alkoxycarbonyl, carboxy, $C_{1-6}$ hydroxyalkyl, $C_{2-6}$ hydroxyalkoxy, ($C_{1-6}$)alkoxy($C_{2-6}$)alkoxy, mono- and di-$C_{1-4}$ alkylamino($C_{2-6}$)alkoxy, $C_{2-10}$ mono (carboxyalkyl)amino, di($C_{2-10}$ carboxyalkyl)amino, $C_{6-14}$ ar($C_{1-6}$) alkoxycarbonyl, $C_{2-6}$ alkynylcarbonyl, $C_{1-6}$ alkylsulfonyl, $C_{2-6}$ alkenylsulfonyl, $C_{2-6}$ alkynylsulfonyl, $C_{6-10}$ arylsulfonyl, $C_{6-10}$ ar($C_{1-6}$) alkylsulfonyl, $C_{1-6}$ alkylsulfinyl, $C_{1-6}$ alkylsulfonamido, $C_{6-10}$ arylsulfonamido, $C_{6-10}$ ar($C_{1-6}$) alkylsulfonamido, amidino, guanidino, $C_{1-6}$ alkyliminoamino, formyliminoamino, $C_{2-6}$ carboxyalkoxy, $C_{2-6}$ carboxyalkyl, carboxyalkylamino, cyano, trifluoromethoxy, perfluoroethoxy and $R^{13}R^{14}NSO_2$—;

$R^{13}$ and $R^{14}$ are independently selected from the group consisting of hydrogen, alkyl, cycloalkyl, alkenyl, alkynyl, aryl, aralkyl, heterocycle, heterocycloalkyl, carboxyalkyl, alkoxycarbonylalkyl, cyano($C_{2-10}$) alkyl, hydroxy($C_{2-10}$)alkyl, alkoxy($C_{2-10}$)alkyl, mono- and di-alkylamino($C_{2-10}$)alkyl, or $R^{13}$ and $R^{14}$ can be taken together with the nitrogen atom to which they are attached to form a three to seven membered ring, optionally containing one or more heteroatoms in addition to said nitrogen, such as oxygen, sulfur, or nitrogen ($NR^{15}$), said ring being preferably saturated, and said ring having one or two optional substituents selected from the group consisting of hydroxy, acyloxy, alkoxy, aryloxy, amino, mono- and di-alkylamino, acylamino, alkyl, cycloalkyl, alkenyl, alkynyl, aryl, aralkyl, heterocycle, heterocycloalkyl, carboxyalkyl, alkoxycarbonylalkyl, cyano($C_{2-10}$)alkyl, hydroxy($C_{2-10}$)alkyl, alkoxy($C_{2-10}$)alkyl, mono- and di-alkylamino($C_{2-10}$)alkyl, carboxy, alkoxycarbonyl, carboxamido, formyl, alkanoyl, aroyl, aralkanoyl, sulfonyl, alkylsulfonyl, alkoxysulfonyl, sulfonamido, phosphonyl, phosphoramido, and phosphinyl, and wherein $R^{15}$ is selected from the group consisting of hydrogen, alkyl, cycloalkyl, alkenyl, alkynyl, aryl, aralkyl, heterocycle, heterocycloalkyl, carboxyalkyl, alkoxycarbonylalkyl, cyano($C_{2-10}$)alkyl, hydroxy ($C_{2-10}$)alkyl, alkoxy($C_{2-10}$)alkyl, mono- and di-alkylamino($C_{2-10}$)alkyl, carboxy, alkoxycarbonyl, carboxamido, formyl, alkanoyl, aroyl, aralkanoyl, sulfonyl, alkylsulfonyl, alkoxysulfonyl, sulfonamido, phosphonyl, phosphoramido, and phosphinyl; and Z is one of —$SO_2O$—, —$OSO_2$—, —$C(R^yR^z)O$— or —$OC(R^yR^z)$—, where $R^y$ and $R^z$ are each hydrogen. Z is most preferably —$SO_2O$—.

Preferred compounds include compounds of Formulae Ia and Ib wherein:

$R^1$ is one of phenyl, naphthyl, pyridyl, thiophenyl, quinolinyl or isoquinolinyl, optionally substituted by one or two of chloro, methoxy, methyl, trifluoromethyl, methylsulfonyl, cyano, nitro, amino or dimethylamino;

Z is —$SO_2O$—;

$R^3$ and $R^4$ are hydrogen or $C_{1-4}$ alkyl, or $R^3$ and $R^4$ may also be taken together to form —CH═CH—CH═CH—;

$R^5$ is one of hydrogen, methyl, methoxy or trifluoromethyl;

$R^6$ is hydrogen;

Y is one of O, $NR^{10}$ or a covalent bond; and $R^{10}$, in each instance, is independently hydrogen, $C_{1-4}$ alkyl, $C_{2-4}$ hydroxyalkyl, $C_{2-4}$ carboxyalkyl, $C_{2-4}$ aminoalkyl, dimethylamino($C_{2-8}$)alkyl, methylamino($C_{2-8}$)alkyl.

Yet another preferred group of compounds include compounds of Formulae Ia and Ib wherein:

$R^1$ is phenyl, substituted by one of alkylsulfonyl, arylsulfonyl and $R^{13}R^{14}NSO_2$—, where $R^{13}$ and $R^{14}$ are independently selected from the group consisting of hydrogen, $C_{1-6}$ alkyl, $C_{3-7}$ cycloalkyl, $C_{2-6}$ alkenyl, $C_{2-6}$ alkynyl, $C_{6-10}$ aryl, $C_{6-10}$ ar($C_{1-4}$)alkyl, pyridyl, pyridyl($C_{1-4}$)alkyl, carboxy($C_{1-6}$)alkyl, $C_{1-4}$ alkoxycarbonyl($C_{1-4}$)alkyl, cyano($C_{2-6}$)alkyl, hydroxy($C_{2-6}$)alkyl, $C_{1-4}$ alkoxy ($C_{2-6}$)alkyl, mono- and di-($C_{1-4}$)alkylamino($C_{2-6}$) alkyl, or $R^{13}$ and $R^{14}$ can be taken together with the nitrogen atom to which they are attached to form a heterocyclic ring selected from the group consisting of N-morpholino, N-piperazinyl (optionally N' substituted with $C_{1-6}$alkyl, $C_{1-6}$ hydroxyalkyl, $C_{6-10}$aryl, $C_{6-10}$ aryl($C_{1-6}$)alkyl, $C_{1-6}$ alkylsulfonyl, $C_{6-10}$ arylsulfonyl, $C_{1-6}$ alkylcarbonyl, morpholino or $C_{6-10}$ arylcarbonyl), N-pyrrolyl, N-piperidinyl, N-pyrrolidinyl, N-dihydropyridyl, and N-indolyl, wherein said heterocyclic ring can be optionally substituted with one or two of hydroxy, $C_{1-8}$ alkanoyloxy, $C_{1-6}$ alkoxy, $C_{6-10}$ aryloxy, amino, mono- and di-$C_{1-6}$ alkylamino, $C_{1-8}$ alkanoylamino, $C_{1-4}$ alkyl, $C_{3-7}$ cycloalkyl, $C_{6-10}$ aryl, $C_{6-10}$ ar($C_{1-4}$)alkyl, heterocycle, heterocycloalkyl, carboxy ($C_{1-6}$)alkyl, $C_{1-4}$ alkoxycarbonyl($C_{1-4}$)alkyl, cyano ($C_{2-6}$)alkyl, hydroxy($C_{2-6}$)alkyl, $C_{1-4}$ alkoxy($C_{2-6}$) alkyl, mono- and di-($C_{1-4}$)alkylamino($C_{2-6}$)alkyl, carboxy, $C_{1-6}$ alkoxycarbonyl, carboxamido, formyl, $C_{1-6}$ alkanoyl, $C_{6-10}$ aroyl, $C_{6-10}$ ar($C_{1-4}$)alkanoyl, sulfonyl, $C_{1-6}$ alkylsulfonyl, $C_{1-6}$ alkoxysulfonyl, sulfonamido, phosphonyl, phosphoramido, or phosphinyl;

Z is one of —SO$_2$O—, —CH$_2$O— or —OCH$_2$—;

R$^3$ and R$^4$ are hydrogen or C$_{1-4}$alkyl, or R$^3$ and R$^4$ may also be taken together to form —CH=CH—CH=CH—;

R$^5$ is one of hydrogen, methyl, methoxy or trifluoromethyl;

R$^6$ is hydrogen;

Y is one of O, NR$^{10}$ or a covalent bond; and

R$^{10}$, in each instance, is independently hydrogen, C$_{1-4}$ alkyl, C$_{2-4}$ hydroxyalkyl, C$_{2-4}$ carboxyalkyl, C$_{2-4}$ aminoalkyl, dimethylamino(C$_{2-8}$)alkyl, methylamino(C$_{2-8}$)alkyl.

The moiety —Z—R$^1$ of Formulae Ia and Ib is attached to the benzene ring in a position ortho-, meta- or para- to Y, with the meta-position being preferred.

Preferred compounds of the present invention are those of Formulae Ia and Ib wherein Y is one of divalent oxygen (—O—), —NR$^{10}$— or a covalent bond, most preferably —O—, and Z is one of —SO$_2$O— or —CH$_2$O—, most preferably —SO$_2$O—.

Preferred values of optional substituents on R$^1$ include hydroxy, nitro, trifluoromethyl, halogen, C$_{1-6}$ alkyl, C$_{1-6}$ alkoxy, C$_{1-6}$ aminoalkyl, C$_{6-10}$ aryl, C$_{6-10}$ ar(C$_{1-6}$)alkoxy, biphenyl(C$_{1-6}$)alkoxy C$_{1-6}$ aminoalkoxy, amino, mono(C$_{1-4}$)alkylamino, di(C$_{1-4}$)alkylamino, C$_{2-6}$ alkoxycarbonylamino, C$_{2-6}$ alkoxycarbonyl, carboxy, C$_{1-6}$ hydroxyalkyl, C$_{2-10}$ mono(carboxyalkyl)amino, bis(C$_{2-10}$ carboxyalkyl)amino, C$_{6-14}$ ar(C$_{1-6}$)alkoxycarbonyl, C$_{2-6}$ alkynylcarbonyl, C$_{1-6}$ alkylsulfonyl, C$_{6-10}$ arylsulfonyl, C$_{2-6}$ alkenylsulfonyl, C$_{2-6}$ alkynylsulfonyl, C$_{1-6}$ alkylsulfinyl, C$_{1-6}$ alkylsulfonamido, amidino, guanidino, C$_{1-6}$ alkyliminoamino, formyliminoamino, C$_{2-6}$ carboxyalkoxy, carboxyalkylamino, cyano, trifluoromethoxy, and perfluoroethoxy.

Additional preferred values of optional substituents on R$^1$ include C$_{1-6}$ alkylsulfonyl, C$_{6-10}$ arylsulfonyl, C$_{6-10}$ ar(C$_{1-6}$) alkylsulfonyl, C$_{6-10}$ arylsulfonamido, C$_{6-10}$ ar(C$_{1-6}$) alkylsulfonamido, N-morpholinosulfonyl, and R$^{13}$R$^{14}$NSO$_2$—, where R$^{13}$ and R$^{14}$ are independently selected from the group consisting of hydrogen, C$_{1-6}$ alkyl, C$_{3-7}$ cycloalkyl, C$_{2-6}$ alkenyl, C$_{2-6}$ alkynyl, C$_{6-10}$ aryl, C$_{6-10}$ ar(C$_{1-4}$)alkyl, pyridyl, pyridyl(C$_{1-4}$)alkyl, carboxy(C$_{1-6}$) alkyl, C$_{1-4}$ alkoxycarbonyl(C$_{1-4}$)alkyl, cyano(C$_{2-6}$)alkyl, hydroxy(C$_{2-6}$)alkyl, C$_{1-4}$ alkoxy(C$_{2-6}$)alkyl, mono- and di-(C$_{1-4}$)alkylamino(C$_{2-6}$)alkyl, or R$^{13}$ and R$^{14}$ can be taken together with the nitrogen atom to which they are attached to form a heterocyclic ring selected from the group consisting of N-morpholinosulfonyl, N-piperazinylsulfonyl (optionally N' substituted with C$_{1-6}$ alkyl, C$_{1-6}$ hydroxyalkyl, C$_{6-10}$ aryl, C$_{6-10}$ aryl(C$_{1-6}$)alkyl, C$_{1-6}$ alkylsulfonyl, C$_{6-10}$ arylsulfonyl, C$_{1-6}$ alkylcarbonyl, morpholino or C$_{6-10}$ arylcarbonyl), N-pyrrolylsulfonyl, N-piperidinylsulfonyl, N-pyrrolidinylsulfonyl, N-dihydropyridylsulfonyl, N-indolylsulfonyl, wherein said heterocyclic ring can be optionally substituted with one or two of hydroxy, C$_{1-8}$ alkanoyloxy, C$_{1-6}$ alkoxy, C$_{6-10}$ aryloxy, amino, mono- and di-C$_{1-6}$ alkylamino, C$_{1-8}$ alkanoylamino, C$_{1-4}$ alkyl, C$_{3-7}$ cycloalkyl, C$_{6-10}$ aryl, C$_{6-10}$ ar(C$_{1-4}$)alkyl, heterocycle, heterocycloalkyl, carboxy(C$_{1-6}$) alkyl, C$_{1-4}$ alkoxycarbonyl(C$_{1-4}$)alkyl, cyano(C$_{2-6}$)alkyl, hydroxy(C$_{2-6}$)alkyl, C$_{1-4}$ alkoxy(C$_{2-6}$)alkyl, mono- and di-(C$_{1-4}$)alkylamino(C$_{2-6}$)alkyl, carboxy, C$_{1-6}$ alkoxycarbonyl, carboxamido, formyl, C$_{1-6}$ alkanoyl, C$_{6-10}$ aroyl, C$_{6-10}$ ar(C$_{1-4}$)alkanoyl, sulfonyl, C$_{1-6}$ alkylsulfonyl, C$_{1-6}$ alkoxysulfonyl, sulfonamido, phosphonyl, phosphoramido, or phosphinyl.

An additional preferred group of compounds are those compounds of Formulae Ia and Ib wherein R$^1$ is heteroaryl or substituted heteroaryl. Preferred R$^1$ heteroaryl groups include pyridyl, pyrazolyl, thiophenyl, chromenyl, benzoxazolyl, benzthiadiazolyl, quinazolinyl, quinolinyl, isoquinolinyl and tetrahydroquinolinyl, with thiophenyl, quinazolinyl, quinolinyl and tetrahydroquinolinyl being more preferred and thiophenyl, isoquinolinyl and quinolinyl especially preferred. Preferred compounds when R$^1$ is substituted heteroaryl include those compounds having one of the heteroaryl groups mentioned as preferred that have one or more, preferably one or two, substituents that are listed in the preceding paragraph. Preferred substituents when R$^1$ is substituted heteroaryl include one or more substituents, preferably 1 to 3 substituents, independently selected from halogen, C$_{1-6}$ alkyl, C$_{1-6}$ alkoxy, amidino, guanidino, carboxyalkoxy, carboxyalkylamino, amino, mono(C$_{1-6}$) alkylamino and/or di(C$_{1-6}$)alkylamino.

Useful values of R$^1$ include phenyl, chlorophenyl, iodophenyl, dichlorophenyl, bromophenyl, trifluoromethylphenyl, methylsulfonylphenyl, di(trifluoromethyl)phenyl, methylphenyl, t-butylphenyl, methoxyphenyl, dimethoxyphenyl, hydroxyphenyl, carboxyphenyl, aminophenyl, methylaminophenyl, n-butylaminophenyl, amidinophenyl, guanidinophenyl, formyliminoaminophenyl, acetimidoylaminophenyl, methoxycarbonylphenyl, ethoxycarbonylphenyl, carboxymethoxyphenyl, naphthyl, hydroxynaphthyl, cyclohexyl, cyclopentyl, 2-propylbutyl, 5-chloro-2-methoxyphenyl, 2-cyanophenyl, 2-(N-hydroxy) aminophenyl, 2-(4-biphenylmethoxy)phenyl, 2-(3-biphenylmethoxy)phenyl, benzyl, 3-(6-(2,3-dihydro-1,1-dioxobenzo[b]thiophene)phenyl, 2-(phenylsulfonyl)phenyl, 2,4-bis(methylsulfonyl)phenyl, and 2-chloro-4-methylsulfonylphenyl. Additional useful values include 8-quinolinyl, 5-methyl-8-quinolinyl, 4-benzo-2,1,3-thiadiazolyl, 5-chloro-2-thiophenyl, 5-chloro-1,3-dimethyl-4-pyrazolyl, pyridyl, isoquinolinyl, and tetrahydroquinolinyl.

Useful values of R$^1$, when R$^1$ is phenyl substituted by R$^{13}$R$^{14}$NSO$_2$— include 2-(N-methyl-phenethylaminosulfonyl)phenyl, bis(2-methoxyethyl) aminosulfonylphenyl, 2-N-methyl-(3,4-dimethoxyphenyl) ethylaminosulfonylphenyl, N-methyl-N-ethoxycarbonylmethyl)aminosulfonylphenyl, 2-(N-methyl-N-(2-(2-pyridyl)ethyl)aminosulfonyl)phenyl, 2-(N-propyl-N-(2-(2-pyridyl)ethyl)aminosulfonyl)phenyl, 2-(N-ethyl-N-(4-pyridylmethyl)aminosulfonyl)phenyl, 2-(N-methyl-N-(4-methoxyphenyl)-aminosulfonyl)phenyl, 2-(N-methyl-N-(4-methoxycarbonylphenyl)aminosulfonyl)phenyl, 2-(N-(2-cyanoethyl)-N-(3-pyridylmethyl)aminosulfonyl)phenyl, 2-(N,N-bis-(2-cyanoethyl)aminosulfonyl)phenyl, 2-(N-(2-ethoxycarbonylethyl)-N-benzyl-aminosulfonyl)phenyl, 2-(N-methyl-N-(2-(4-pyridyl)ethyl)aminosulfonyl)phenyl, 2-(N-(ethoxycarbonylmethyl)-N-(2-pyridylmethyl) aminosulfonyl) phenyl, 2-(N,N-,bis(ethoxycarbonylmethyl) aminosulfonyl)phenyl, 2-(N,N-bis-(carboxymethyl) aminosulfonyl)phenyl, 2-(N-methyl-N-(4-carboxyphenyl) aminosulfonyl)phenyl, 2-(N-(2-carboxyethyl)-N-benzylaminosulfonyl)phenyl, 2-(N-(2-cyanoethyl)-N-(2-furanylmethyl)aminosulfonyl)phenyl, 2-(N-ethyl-N-(1-benzyl-3-pyrrolidinyl)aminosulfonyl)phenyl, 2-(N-benzyl-N-(2-(N,N-dimethylamino)ethyl)aminosulfonyl)phenyl, 2-(N-methyl-N-(1-methyl-4-piperidinyl)aminosulfonyl) phenyl, 2-(N-methyl-N-(3-pyridylmethyl)aminosulfonyl) phenyl, 2-(N-ethyl-N-(2-(N,N-dimethylamino)ethyl) aminosulfonyl)phenyl, 2-(2-(4-morpholinyl) ethylaminosulfonyl)phenyl, 2-(N-methyl-N-(2-(N,N-dimethylamino)ethyl)amino sulfonyl)phenyl, N-ethyl-3,4-

(methylenedioxy)anilinosulfonylphenyl, 2-(N-methyl-N-(3-(N,N-dimethylamino)propyl)aminosulfonyl)phenyl, and 2-(4-pyridylmethyl-aminosulfonyl)phenyl.

Further useful values of $R^1$, when $R^1$ is phenyl substituted by $R^{13}R^{14}NSO_2$— include 2-morpholinylsulfonylphenyl, 2-(acetylpiperazinylsulfonyl)phenyl, 2-(4-ethyloxycarbonyl)piperidinylsulfonyl, 2-(4-carboxyl)piperidinylsulfonylphenyl, 3-ethoxycarbonyl-1-piperidinosulfonyl)phenyl, 3-carboxypiperidinosulfonyl)phenyl, 2-methoxycarbonyl-1-pyrrolidinosulfonyl)phenyl, 2-carboxy-1-pyrrolidinosulfonyl)phenyl, 2-(4-methylsulfonylpiperazin-1-ylsulfonyl)phenyl, 2-(4-(2-pyrimidinyl)piperazin-1-ylsulfonyl)phenyl, 2-(4-ethylpiperazin-1-ylsulfonyl)phenyl, 2-(4-(piperidin-1-yl)piperidin-1-ylsulfonyl)phenyl, 2-(4-(ethoxycarbonylmethyl)piperazin-1-ylsulfonyl)phenyl, 2-(4-(carboxymethyl)piperazin-1-ylsulfonyl)phenyl, 2-(4-(2-pyridyl)piperazinylsulfonyl)phenyl, 2-(4-phenylpiperazinylsulfonyl)phenyl, 2-(4-benzylpiperazinylsulfonyl)phenyl, 2-(4-(2-methoxyphenyl)piperazinylsulfonyl)phenyl, 2-(4-methylpiperazinylsulfonyl)phenyl, 2-(4-(pyrrolidin-1-yl)piperidin-1-ylsulfonyl)phenyl, and 2-(4-ethoxycarbonyl-1-piperazinylsulfonyl)phenyl.

The groups $R^3$, $R^4$, $R^5$ and $R^6$ in Formulae Ia and Ib substitute for any remaining hydrogen atoms on the benzene ring after allowing for attachment of the moiety —Z—$R^1$. Preferred compounds are those where $R^3$, $R^4$, $R^5$ and $R^6$ are independently hydrogen, $C_{1-4}$ alkyl, $C_{4-7}$cycloalkyl, $C_{6-14}$ aryl, especially $C_{6-10}$ aryl, $C_{6-10}$ ar($C_{1-4}$)alkyl, trifluoromethyl, halogen, hydroxyalkyl, cyano, nitro, carboxamide, carboxy, alkoxycarbonyl, carboxymethyl, alkoxycarbonylmethyl, or cycloalkyloxycarbonyl.

Alternatively, $R^3$ and $R^4$, when attached to adjacent carbon atoms on the benzene ring, are one of —CH=CH—CH=CH— or —(CH$_2$)$_q$—, where q is from 2 to 6, thereby forming a fused ring. Preferred values of $R^3$ together with $R^4$ include —CH=CH—CH=CH—, —CH$_2$—CH$_2$—CH$_2$— and —CH$_2$—CH$_2$—CH$_2$—CH$_2$—. When $R^3$ and $R^4$ together form a fused ring, $R^5$ and $R^6$ are preferably hydrogen.

Useful values of $R^3$, $R^4$, $R^5$ and $R^6$ include hydrogen, methyl, ethyl, chloro, bromo, trifluoromethyl, hydroxymethyl, methoxy, ethoxy, carboxamide, nitro, phenyl, cyclopropyl, hydroxy, isopropyl, methoxycarbonyl, ethoxycarbonyl and benzyl. Useful values of $R^3$ and $R^4$ also include $R^3$ and $R^4$ together forming —CH=CH—CH=CH— or —CH$_2$—CH$_2$—CH$_2$— and $R^5$ and $R^6$ being hydrogen.

Another group of preferred compounds of Formulae Ia and Ib are those wherein:

$R^3$, $R^4$, $R^5$ and $R^6$ are independently one of hydrogen, $C_{1-4}$ alkyl, $C_{3-8}$ cycloalkyl, phenyl, benzyl, trifluoromethyl, halogen, hydroxy($C_{1-4}$)alkyl, cyano, nitro, carboxamido, carboxy, $C_{1-4}$ alkoxycarbonyl, $C_{1-4}$ alkoxymethyl or $C_{1-4}$ alkoxy; or alternatively, $R^4$ and $R^3$, when present on adjacent carbon atoms, may also be taken together to form one of —CH=CH—CH=CH— or —(CH$_2$)$_q$—, where q is from 2 to 6, and $R^5$ and $R^6$ are as defined above;

Y is one of —O—, —S—, —NR$^{10}$—, or a covalent bond; and $R^{10}$, in each instance, is independently hydrogen, $C_{1-6}$ alkyl, benzyl, phenyl, $C_{2-10}$ hydroxyalkyl, $C_{2-10}$ aminoalkyl, $C_{1-4}$ monoalkylamino($C_{2-8}$)alkyl, $C_{1-4}$ dialkylamino($C_{2-8}$)alkyl or $C_{2-10}$ carboxyalkyl.

In this preferred embodiment, $R^1$ can be one of $C_{6-10}$ aryl, pyridinyl, thiophenyl (i.e., thiophene), quinazolinyl, quinolinyl or tetrahydroquinolinyl, any of which is optionally substituted by one or two of hydroxy, nitro, trifluoromethyl, halogen, $C_{1-6}$ alkyl, $C_{1-6}$ alkoxy, $C_{1-6}$ aminoalkyl, $C_{1-6}$ aminoalkoxy, amino, mono($C_{1-4}$)alkylamino, di($C_{1-4}$)alkylamino, $C_{2-6}$ alkoxycarbonylamino, $C_{2-6}$ alkoxycarbonyl, carboxy, $C_{1-6}$ hydroxyalkyl, $C_{2-6}$ hydroxyalkoxy, $C_{2-10}$ mono(carboxyalkyl)amino, bis($C_{2-10}$ carboxyalkyl)amino, $C_{6-14}$ ar($C_{1-6}$) alkoxycarbonyl, $C_{2-6}$ alkynylcarbonyl, $C_{1-6}$ alkylsulfonyl, $C_{2-6}$ alkenylsulfonyl, $C_{2-6}$ alkynylsulfonyl, $C_{2-6}$ alkylsulfinyl, $C_{1-6}$ alkylsulfonamido, amidino, guanidino, $C_{1-6}$ alkyliminoamino, formyliminoamino, $C_{2-6}$ carboxyalkoxy, $C_{2-6}$ carboxyalkyl, carboxyalkylamino, cyano, trifluoromethoxy, and perfluoroethoxy.

Preferred values of $R^{10}$ in Formulae Ia and Ib include hydrogen, $C_{1-6}$ alkyl, $C_{6-10}$ ar($C_{1-6}$)alkyl, $C_{6-10}$ aryl, $C_{2-10}$ hydroxyalkyl $C_{2-10}$ aminoalkyl, $C_{2-7}$ carboxyalkyl, mono ($C_{1-4}$ alkyl)amino($C_{1-8}$)alkyl, and di($C_{1-4}$ alkyl)amino ($C_{1-8}$)alkyl. Suitable values of $R^{10}$ include methyl, ethyl, propyl, n-butyl, benzyl, phenylethyl, 2-hydroxyethyl, 3-hydroxypropyl, 4-hydroxybutyl, 2-aminoethyl, 2-carboxymethyl, 3-carboxyethyl, 4-carboxypropyl and 2-(dimethylamino)ethyl.

Preferred values of $R^a$, $R^b$ and $R^c$ in Formulae Ia and Ib are hydrogen, hydroxy, $C_{1-6}$alkyl, $C_{1-6}$ alkoxy, cyano or —CO$_2$R$^w$, where R$^w$, in each instance, is preferably one of $C_{1-4}$alkyl, $C_{4-7}$cycloalkyl or benzyloxycarbonyl. Suitable values of $R^a$, $R^b$ and $R^c$ include hydrogen, methyl, ethyl, propyl, n-butyl, hydroxy, methoxy, ethoxy, cyano, —CO$_2$CH$_3$, —CO$_2$CH$_2$CH$_3$ and —CO$_2$CH$_2$CH$_2$CH$_3$. In the most preferred embodiments, $R^a$, $R^b$ and $R^c$ are each hydrogen.

Also preferred at $R^a$, $R^b$ and $R^c$ is the group —CO$_2$R$^w$, where R$^w$ is one of

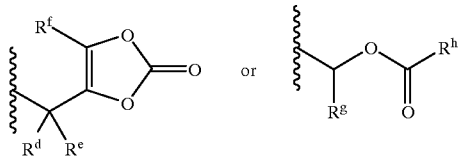

where $R^d$–$R^h$ are defined as above. When $R^a$, $R^b$ and $R^c$ are —CO$_2$R$^w$, where R$^w$ is one of these moieties, the resulting compounds are prodrugs that possess desirable formulation and bioavailability characteristics. A preferred value for each of $R^d$, $R^e$ and $R^f$ is hydrogen, $R^f$ is methyl, and preferred values for $R^h$ include benzyl and tert-butyl.

Preferred values of m, m', n, n', j, and j' in Formulae Ia and Ib are 0 or 1, provided that m, m', n, n', j, and j' are not all zero. The most preferred value for each n, n', j, j', and m is 1; the most preferred value for m' is zero.

Compounds of the present invention also include compounds of Formula II:

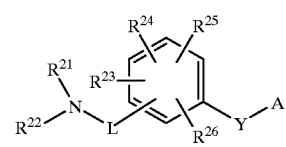

II or a solvate, hydrate or pharmaceutically acceptable salt thereof; wherein:

A is one of

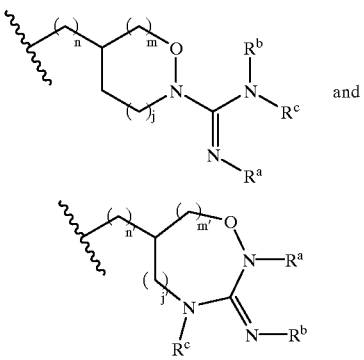

and

Thus, the compounds of Formula II are represented by Formulae IIa and IIb:

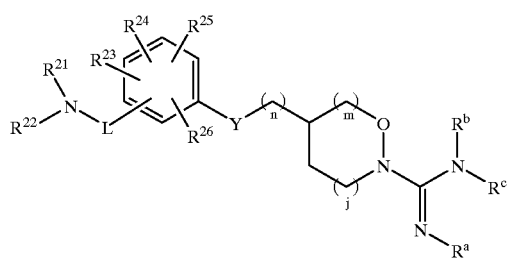

IIa

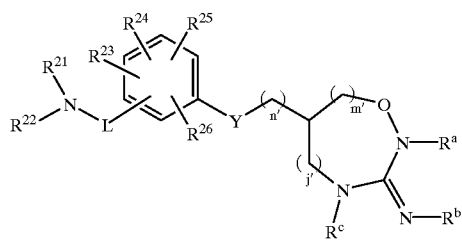

IIb or a solvate, hydrate or pharmaceutically acceptable salt thereof.

For each of Formulae II, IIa and IIb, the following values apply:

L represents —C(O)—, C($R^{2Y}R^{2Z}$), or —$SO_2$—;

$R^{2Y}$ and $R^{2Z}$ are each independently one of hydrogen, alkyl, cycloalkyl, aryl, aralkyl, hydroxyalkyl, carboxyalkyl, aminoalkyl, monoalkylaminoalkyl, dialkylaminoalkyl or carboxy;

$R^{21}$ represents a group:

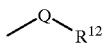

$R^{22}$ represents a group:

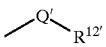

or $R^{21}$ and $R^{22}$ can be taken together with the nitrogen atom to which they are attached to form a three to seven membered ring, either of which contains an additional nitrogen or oxygen atom, and which is optionally benzo- or pyrido-fused, said ring being preferably saturated, and said ring having one or two optional substituents on either a ring carbon or nitrogen selected from the group consisting of halogen, hydroxy, acyloxy, alkoxy, aryloxy, alkyl, cycloalkyl, alkenyl, alkynyl, aryl, aralkyl, heteroaryl, heteroar($C_{1-4}$)alkyl, carboxyalkyl, alkoxycarbonylalkyl, hydroxyalkoxyalkyl, cyano($C_{2-10}$)alkyl, hydroxy($C_{2-10}$)alkyl, alkoxy($C_{2-10}$)alkyl, alkoxyalkyl, mono- and di-alkylamino($C_{2-10}$)alkyl, carboxy, alkoxycarbonyl, carboxamido, formyl, alkanoyl, aroyl, aralkanoyl, sulfonyl, alkylsulfonyl, alkoxysulfonyl, and $NR^{13}R^{14}$ (when C-substituted);

$R^{12}$ and $R^{12'}$ independently represent hydrogen, $C_{3-7}$ cycloalkyl, $C_{3-7}$ cycloalkenyl, $C_{3-7}$ heterocycloalkyl, $C_{3-7}$ heterocycloalkenyl, aryl, or heteroaryl, which groups are optionally substituted with $C_{1-6}$ alkyl or hydroxy, or $R^{12}$ and $R^{12'}$ independently represent diarylmethyl, diheteroarylmethyl, dicycloalkylmethyl or (aryl)(heteroaryl)CH—;

Q and Q' independently represent a bond, a $C_{1-6}$ alkyl chain, a $C_{3-6}$ alkenyl chain, or a $C_{3-6}$ alkynyl chain, where one or two nitrogen, oxygen, or sulfur atoms may be optionally contained within each chain, and the chains are optionally substituted by one or more groups selected from halogen, hydroxy, CN, $C_{1-6}$ alkyl, $C_{1-6}$ alkoxy, $C_{1-6}$ alkoxy($C_{1-6}$)alkyl, $C_{1-6}$ acyloxy, $NR^{13}R^{14}$, $NHCOR^{15}$, $NHSO_2R^{16}$, $COR^{15}$, $CO_2R^{15}$, $CONR^{13}R^{14}$, and $SO_2NR^{17}R^{18}$;

$R^{13}$–$R^{16}$ represent hydrogen, $C_{1-6}$ alkyl, $C_{3-7}$ cycloalkyl, $C_{2-6}$ alkenyl, $C_{2-6}$ alkynyl, $C_{6-10}$ aryl, mono- or di-hydroxy($C_{6-10}$)aryl, $C_{6-10}$ ar($C_{1-4}$)alkyl, pyridyl, pyridyl($C_{1-4}$)alkyl, carboxy($C_{1-6}$)-alkyl, $C_{1-4}$ alkoxycarbonyl($C_{1-4}$)alkyl, cyano($C_{2-6}$)alkyl, hydroxy ($C_{2-6}$)alkyl, $C_{1-4}$ alkoxy($C_{2-6}$)alkyl, mono- and di-($C_{1-4}$)alkylamino($C_{2-6}$)alkyl;

or $R^{13}$ and $R^{14}$ form a $C_{3-7}$ heterocycloalkyl ring, or $R^{16}$ additionally may represent trifluoromethyl;

$R^{17}$ and $R^{18}$ are independently selected from the group consisting of hydrogen, $C_{1-6}$ alkyl, $C_{3-7}$ cycloalkyl, $C_{2-6}$ alkenyl, $C_{2-6}$ alkynyl, $C_{6-10}$ aryl, $C_{6-10}$ ar($C_{1-4}$) alkyl, pyridyl, pyridyl($C_{1-4}$)alkyl, carboxy($C_{1-6}$)alkyl, $C_{1-4}$ alkoxycarbonyl-($C_{1-4}$)alkyl, cyano($C_{2-6}$)alkyl, hydroxy($C_{2-6}$)alkyl, $C_{1-4}$ alkoxy($C_{2-6}$)alkyl, and mono- and di-($C_{1-4}$)alkylamino($C_{2-6}$)alkyl, or $R^{17}$ and $R^{18}$ can be taken together with the nitrogen atom to which they are attached to form a heterocyclic ring selected from the group consisting of N-morpholino, N-piperazinyl (optionally N' substituted with $C_{1-6}$ alkyl, $C_{1-6}$ hydroxyalkyl, $C_{6-10}$ aryl, $C_{6-10}$ aryl($C_{1-6}$)alkyl, $C_{1-6}$ alkylsulfonyl, $C_{6-10}$ arylsulfonyl, $C_{1-6}$ alkylcarbonyl, morpholino or $C_{6-10}$ arylcarbonyl), N-pyrrolyl, N-piperidinyl, N-pyrrolidinyl, N-dihydropyridyl, and N-indolyl, wherein said heterocyclic ring can be optionally C-substituted.

$R^{23}$, $R^{24}$, $R^{25}$ and $R^{26}$ are each independently one of hydrogen, alkyl, cycloalkyl, alkenyl, alkynyl, optionally substituted aryl, optionally substituted aralkyl, optionally substituted heteroaryl, trifluoromethyl, halogen, hydroxyalkyl, cyano, nitro, carboxamido, —$CO_2R^x$, —$CH_2OR^x$ or —$OR^x$, or when present on adjacent carbon atoms, $R^{23}$ and $R^{24}$ may also be taken together to form one of —CH═CH—CH═CH— or —(CH$_2$)$_q$—, where q is from 2 to 6, and $R^{25}$ and $R^{26}$ are defined as above;

$R^x$, in each instance, is independently one of hydrogen, alkyl or cycloalkyl wherein said alkyl or cycloalkyl groups may optionally have one or more unsaturations;

Y is one of —O—, —NR$^{19}$—, —S—, —CHR$^{19}$— or a covalent bond;

R$^{19}$, in each instance, is independently hydrogen, C$_{1-6}$ alkyl, benzyl, phenyl, C$_{2-10}$ hydroxyalkyl, C$_{2-10}$ aminoalkyl, C$_{1-4}$ monoalkylamino(C$_{2-8}$)alkyl, C$_{1-4}$ dialkylamino(C$_{2-8}$)alkyl or C$_{2-10}$ carboxyalkyl;

R$^a$, R$^b$ and R$^c$ are independently hydrogen, alkyl, hydroxy, alkoxy, aryloxy, aralkoxy, alkoxycarbonyloxy, cyano or —CO$_2$R$^w$, where R$^w$ is alkyl, cycloalkyl, phenyl, benzyl,

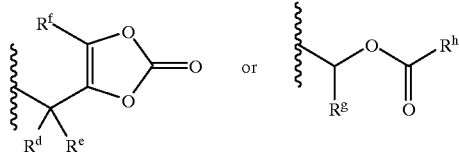

where R$^d$ and R$^e$ are independently hydrogen, C$_{1-6}$ alkyl, C$_{2-6}$ alkenyl or phenyl, R$^f$ is hydrogen, C$_{1-6}$ alkyl, C$_{2-6}$ alkenyl or phenyl, R$^g$ is hydrogen, C$_{1-6}$ alkyl, C$_{2-6}$ alkenyl or phenyl, and R$^h$ is aralkyl or C$_{1-6}$ alkyl;

n and n' are each from zero to 4, preferably zero to 2;

m and m' are each from zero to 4, preferably zero to 2; and j and j' are each from zero to 4, preferably zero to 2;

provided that n, n', m, m', j, and j' are not all zero.

Preferred values of R$^a$, R$^b$, R$^c$, m, m', n, n', j, and j' in Formulae IIa and IIb are the same as those defined for Formulae Ia and Ib above.

Referring to Formulae IIa and IIb, where R$^{22}$ represents a group

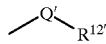

Q' is suitably C$_{3-6}$ alkenyl, e.g., alkyl, or C$_{1-6}$ alkyl, e.g., methyl, ethyl, propyl or pentyl, which optionally contains an oxygen group within the chain and is optionally substituted by a group selected from hydroxy, C$_{1-6}$ alkoxy, NHSO$_2$R$^{16}$, CO$_2$R$^{15}$, CONR$^{13}$R$^{14}$, or SO$_2$NR$^{17}$R$^{18}$, and R$^{12'}$ is suitably hydrogen, C$_{3-7}$ heterocycloalkyl, e.g., pyrrolidine or morpholine, aryl, e.g., phenyl which is optionally substituted by CO$_2$R$^{15}$, or heteroaryl, e.g., oxadiazole optionally substituted by hydroxy, triazole, or tetrazole optionally substituted by C$_{1-6}$ alkyl. Referring to the general Formulae IIa and IIb, where R$^{21}$ represents a group

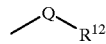

Q is suitably a bond or C$_{1-6}$ alkyl group, e.g., methyl, isopropyl or isobutyl, and R$^{12}$ suitably represents hydrogen, C$_{3-7}$ cycloalkyl, aryl, or heteroaryl. When Q represents a bond, R$^{12}$ is preferably optionally substituted phenyl, C$_{3-7}$ cycloalkyl, e.g., cyclobutyl, cyclopentyl or cyclohexyl, diphenylmethyl or dicyclohexylmethyl. When Q represents a C$_{1-4}$ alkyl group, R$^{12}$ is preferably hydrogen, cycloalkyl, e.g., cyclohexyl, or heteroaryl, e.g., thienyl or furyl.

Particularly preferred combinations of R$^{21}$ and R$^{22}$ include:

(A) R$^{21}$ and R$^{22}$ are taken together with the nitrogen to which they are attached to form a C$_{3-7}$ heterocycloalkyl or C$_{3-7}$ heterocycloalkenyl group, optionally benzo fused and optionally including an oxygen atom or an additional nitrogen atom, and which may be optionally substituted by C$_{1-6}$ alkyl, hydroxy, C$_{1-4}$ alkoxy, C$_{2-6}$ alkoxycarbonyl, formyl, (C$_{6-10}$)ar(C$_{1-4}$)alkyl, C$_{6-10}$ aryl, pyridyl, hydroxyalkoxyalkyl, halogen, or NR$^{13}$R$^{14}$; or (B) R$^{21}$ is C$_{3-7}$ cycloalkyl or C$_{3-7}$ cycloalkenyl, either of which is optionally substituted by C$_{1-6}$ alkyl, hydroxy, C$_{1-4}$ alkoxy, halogen, carboxylic acid, a C$_{1-4}$ carboxylic acid ester group, or NR$^{13}$R$^{14}$, and R$^{22}$ is C$_{3-6}$ alkenyl, or C$_{3-6}$ alkynyl, either of which is optionally substituted by C$_{1-6}$ alkyl, hydroxy, C$_{1-4}$ alkoxy, halogen, carboxylic acid, a C$_{1-4}$ carboxylic acid ester group, or NR$^{13}$R$^{14}$; or (C) R$^{21}$ is C$_{3-7}$ heterocycloalkyl(C$_{1-6}$)alkyl, C$_{3-7}$ heterocycloalkenyl(C$_{1-6}$)alkyl, heteroaryl(C$_{1-6}$)alkyl, C$_{3-7}$ heterocycloalkyl(C$_{3-6}$)alkenyl, C$_{3-7}$ heterocycloalkenyl(C$_{3-6}$)alkenyl, heteroaryl(C$_{3-6}$)alkenyl, C$_{3-7}$ heterocycloalkyl(C$_{3-6}$)alkynyl, C$_{3-7}$ heterocycloalkenyl(C$_{3-6}$)alkynyl, heteroaryl(C$_{3-6}$)alkynyl, di(C$_{5-10}$ aryl)(C$_{1-3}$)alkyl, di(C$_{3-8}$ cycloalkyl)(C$_{1-3}$)alkyl or di(C$_{3-8}$ cycloalkenyl)(C$_{1-3}$)alkyl, any of which is optionally substituted by C$_{1-6}$ alkyl, hydroxy, C$_{1-4}$ alkoxy, halogen, carboxylic acid, a C$_{1-4}$ carboxylic acid ester group, or NR$^{13}$R$^{14}$; and R$^{22}$ is a group

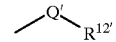

where R$^{12'}$ and Q' have the values and preferred values defined above.

R$^{23}$ can represent hydrogen, C$_{1-3}$ alkyl, halogen, or C$_{1-2}$ alkoxy. R$^{23}$ is preferably C$_{1-3}$ alkyl, e.g., methyl, or halogen, e.g., chlorine or bromine.

R$^{24}$, R$^{25}$, and R$^{26}$ can independently represent hydrogen, or halogen. R$^{24}$, R$^{25}$, and R$^{26}$ are preferably hydrogen, or halogen, e.g., fluorine.

Preferred values of Y are divalent oxygen (—O—), —NR$^{19}$— or a covalent bond, most preferably —O—.

Preferred values of R$^{19}$ are hydrogen, C$_{1-6}$ alkyl and C$_{3-6}$ cycloalkyl.

Specific compounds within the scope of the invention include the following:

3-[(2-amidino(1,2-oxazaperhydroin-5-yl))methoxy]-5-methylphenyl 2-(methylsulfonyl)benzenesulfonate;

3-[(2-amidino(1,2-oxazaperhydroin-5-yl))methoxy]-5-chlorophenyl 2-(methylsulfonyl)benzenesulfonate;

3-[(2-amidino(1,2-oxazaperhydroin-5-yl))methoxy]-5-methylphenyl 2-(methoxy)benzenesulfonate;

3-[(2-amidino(1,2-oxazaperhydroin-5-yl))methoxy]-5-methylphenyl quinolinyl-8-sulfonate;

3-[(2-amidino(1,2-oxazaperhydroin-5-yl))methoxy]-5-methylphenyl 5-chloro-2-(methoxy)benzenesulfonate;

3-[(2-amidino(1,2-oxazaperhydroin-5-yl))methoxy]-5-methylphenyl 5-chlorothiophenyl-2-sulfonate;

3-[(2-amidino(1,2-oxazaperhydroin-5-yl))methoxy]-5-methylphenyl 2-cyanobenzenesulfonate;

3-[(2-amidino(1,2-oxazaperhydroin-5-yl))methoxy]-5-methylphenyl 2-(methylsulfonyl)benzenesulfonate;

3-[(2-amidino(1,2-oxazaperhydroin-5-yl))methoxy]-5-methylphenyl 2-(morpholinylsulfonyl) benzenesulfonate;

3-[(2-amidino(1,2-oxazaperhydroin-5-yl))methoxy]-5-methylphenyl 2-(N-methylphenethylaminosulfonyl) benzenesulfonate;

3-[(2-amidino(1,2-oxazaperhydroin-5-yl)))methoxy]-5-methylphenyl 2-[(4-ethyloxycarbonyl)piperidinylsulfonyl]benzenesulfonate;

3-[(2-amidino(1,2-oxazaperhydroin-5-yl)))methoxy]-5-methylphenyl 3-[(2,4-bis(methylsulfonyl)] benzenesulfonate;

3-[(2-amidino(1,2-oxazaperhydroin-5-yl)))methoxy]-5-methylphenyl 6-[(2,3-dihydro-1,1-dioxobenzo[b]thiophene)]benzenesulfonate;

3-[(2-amidino(1,2-oxazaperhydroin-5-yl)))methoxy]-5-methylphenyl 2-[(4-biphenylmethoxy)]benzenesulfonate;

3-[(2-amidino(1,2-oxazaperhydroin-5-yl)))methoxy]-5-methylphenyl N-ethyl-3,4-[(methylenedioxy)anilinosulfonyl]benzenesulfonate;

3-[(2-amidino(1,2-oxazaperhydroin-5-yl)))methoxy]-5-methylphenyl 3-ethoxycarbonyl-1-(piperidinosulfonyl)benzenesulfonate;

3-[(2-amidino(1,2-oxazaperhydroin-5-yl)))methoxy]-5-methylphenyl 2-methoxycarbonyl-1-pyrrolidinosulfonyl-benzenesulfonate;

3-[(2-amidino(1,2-oxazaperhydroin-5-yl)))methoxy]-5-methylphenyl 2-(N-propyl-N-(2-(2-pyridyl)ethyl)aminosulfonyl)benzenesulfonate;

3-[(2-amidino(1,2-oxazaperhydroin-5-yl)))methoxy]-5-methylphenyl 2-(N,N-bis-(2-cyanoethyl)aminosulfonyl)benzenesulfonate;

3-[(2-amidino(1,2-oxazaperhydroin-5-yl)))methoxy]-5-methylphenyl 2-(N-(2-carboxyethyl)-N-benzylaminosulfonyl)benzenesulfonate;

3-[(2-amidino(1,2-oxazaperhydroin-5-yl)))methoxy]-5-methylphenyl 2-(4-(carboxymethyl)piperazin-N-1-ylsulfonyl)benzenesulfonate;

3-[(2-amidino(1,2-oxazaperhydroin-5-yl)))methoxy]-5-methylphenyl 2-(N-(2-cyanoethyl)-N-(2-furanylmethyl) aminosulfonyl)benzenesulfonate;

3-[(2-amidino(1,2-oxazaperhydroin-5-yl)))methoxy]-5-methylphenyl 2-(N-ethyl-N-(1-benzyl-3-pyrrolidinyl)aminosulfonyl)benzenesulfonate;

5-{[5-chloro-3-(N-cyclopentyl-N-prop-2-enylcarbamoyl)phenoxy]methyl}-1,2-oxazaperhydroine-2-carboxamidine;

5-{[5-chloro-3-(4-benzylpiperidinylcarbonyl)phenoxy]methyl}-1,2-oxazaperhydroine-2-carboxamidine;

5-{[5-chloro-3-(N,N-bis[2-methoxyethyl]aminocarbonyl)phenoxy]methyl}-1,2-oxazaperhydroine-2-carboxamidine;

5-{[5-chloro-3-(N-methyl-N-[3-pyridylmethyl]-aminocarbonyl)phenoxy]methyl}-1,2-oxazaperhydroine-2-carboxamidine;

5-{[5-chloro-3-(N-[2-m dimethylamino ethyl]-N-ethylaminocarbonyl)phenoxy]methyl}-1,2-oxazaperhydroine-2-carboxamidine;

5-{[5-chloro-3-(4-formylpiperazinylcarbonyl)phenoxy]methyl}-1,2-oxazaperhydroine-2-carboxamidine;

5-{[5-chloro-3-(4-benzylpiperazinylcarbonyl)phenoxy]methyl}-1,2-oxazaperhydroine-2-carboxamidine;

5-{[5-chloro-3-(2-[1,2,3,4-tetrahydro]-isoquinolinylcarbonyl)phenoxy]methyl}-1,2-oxazaperhydroine-2-carboxamidine;

5-{[5-chloro-3-(azaperhydroepinylcarbonyl)phenoxy]methyl}-1,2-oxazaperhydroine-2-carboxamidine;

as well as pharmaceutically acceptable salts thereof, for example the hydrochloride, acetate, and trifluoroacetate salts thereof. Structures for these compounds are provided in the pages prior to the claims.

It is also to be understood that the present invention is considered to include stereoisomers as well as optical isomers, e.g. mixtures of enantiomers, as well as individual enantiomers and diastereomers, which arise as a consequence of structural asymmetry in selected compounds of the present series.

The compounds of Formulae I and II may also be solvated, especially hydrated. Hydration may occur during manufacturing of the compounds or compositions comprising the compounds, or the hydration may occur over time due to the hygroscopic nature of the compounds.

Certain compounds within the scope of Formulae I and II are derivatives referred to as prodrugs. The expression "prodrug" denotes a derivative of a known direct acting drug, which derivative has enhanced delivery characteristics and therapeutic value as compared to the drug, and is transformed into the active drug by an enzymatic or chemical process; see Notari, R. E., "Theory and Practice of Prodrug Kinetics," *Methods in Enzymology*, 112:309–323 (1985); Bodor, N., "Novel Approaches in Prodrug Design," *Drugs of the Future*, 6(3):165–182 (1981); and Bundgaard, H., "Design of Prodrugs: Bioreversible-Derivatives for Various Functional Groups and Chemical Entities," in *Design of Prodrugs* (H. Bundgaard, ed.), Elsevier, N.Y. (1985). Useful prodrugs are those where $R^a$, $R^b$ and/or $R^c$ are —$CO_2R^w$, where $R^w$ is defined above. See, U.S. Pat. No. 5,466,811 and Saulnier et al., *Bioorg. Med. Chem. Lett.* 4:1985–1990 (1994).

When any variable occurs more than one time in any constituent or in Formulae I and II, its definition on each occurrence is independent of its definition at every other occurrence. Also, combinations of substituents and/or variables are permissible only if such combinations result in stable compounds.

The term "alkyl" as employed herein by itself or as part of another group refers to both straight and branched chain radicals of up to 12 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl. Preferred alkyl groups have 1 to 6 carbon atoms.

The term "alkenyl" is used herein to mean a straight or branched chain radical of 2–20 carbon atoms, unless the chain length is limited thereto, including, but not limited to, ethenyl, 1-propenyl, 2-propenyl, 2-methyl-1-propenyl, 1-butenyl, 2-butenyl, and the like. Preferably, the alkenyl chain is 2 to 10 carbon atoms in length, more preferably, 2 to 8 carbon atoms in length most preferably from 2 to 4 carbon atoms in length.

The term "alkynyl" is used herein to mean a straight or branched chain radical of 2–20 carbon atoms, unless the chain length is limited thereto, wherein there is at least one triple bond between two of the carbon atoms in the chain, including, but not limited to, acetylene, 1-propylene, 2-propylene, and the like. Preferably, the alkynyl chain is 2 to 10 carbon atoms in length, more preferably, 2 to 8 carbon atoms in length, most preferably from 2 to 4 carbon atoms in length.

In all instances herein where there is an alkenyl or alkynyl moiety as a substituent group, the unsaturated linkage, i.e., the vinylene or acetylene linkage is preferably not directly attached to a nitrogen, oxygen or sulfur moiety.

The term "alkoxy" is used herein to mean a straight or branched chain radical of 1 to 20 carbon atoms, unless the chain length is limited thereto, bonded to an oxygen atom, including, but not limited to, methoxy, ethoxy, n-propoxy, isopropoxy, and the like. Preferably the alkoxy chain is 1 to 10 carbon atoms in length, more preferably 1 to 8 carbon atoms in length.

The term "aryl" as employed herein by itself or as part of another group refers to monocyclic or bicyclic aromatic groups containing from 6 to 12 carbons in the ring portion, preferably 6–10 carbons in the ring portion, such as phenyl, naphthyl or tetrahydronaphthyl.

The term "heteroaryl" as employed herein refers to groups having 5 to 14 ring atoms; 6, 10 or 14 π electrons shared in a cyclic array; and containing carbon atoms and 1, 2 or 3 oxygen, nitrogen or sulfur heteroatoms (where examples of heteroaryl groups are: thienyl, benzo[b]thienyl, naphtho[2,3-b]thienyl, thianthrenyl, furyl, pyranyl, isobenzofuranyl, benzoxazolyl, chromenyl, xanthenyl, phenoxathiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinazolinyl, cinnolinyl, pteridinyl, 4αH-carbazolyl, carbazolyl, β-carbolinyl, phenanthridinyl, acridinyl, perimidinyl, phenanthrolinyl, phenazinyl, isothiazolyl, phenothiazinyl, isoxazolyl, furazanyl and phenoxazinyl groups).

The term "aralkyl" or "arylalkyl" as employed herein by itself or as part of another group refers to $C_{1-6}$alkyl groups as discussed above having an aryl substituent, such as benzyl, phenylethyl or 2-naphthylmethyl.

The term "cycloalkyl" as employed herein by itself or as part of another group refers to cycloalkyl groups containing 3 to 9 carbon atoms. Typical examples are cyclopropyl, cyclobutyl, cyclopentyl, cyclohexyl, cycloheptyl, cyclooctyl and cyclononyl.

The terms "alkoxy" refers to any of the above alkyl groups linked to an oxygen atom.

The term "halogen" or "halo" as employed herein by itself or as part of another group refers to chlorine, bromine, fluorine or iodine with chlorine being preferred.

The term "monoalkylamine" as employed herein by itself or as part of another group refers to an amino group which is substituted with one alkyl group having from 1 to 6 carbon atoms.

The term "dialkylamine" as employed herein by itself or as part of another group refers to an amino group which is substituted with two alkyl groups, each having from 1 to 6 carbon atoms The term "hydroxyalkyl" as employed herein refers to any of the above alkyl groups substituted by one or more hydroxyl moieties.

The term "carboxyalkyl" as employed herein refers to any of the above alkyl groups substituted by one or more carboxylic acid moieties.

The term "heterocyclic" is used herein to mean a saturated or wholly or partially unsaturated 3–7 membered monocyclic, or 7–10 membered bicyclic ring system, which consists of carbon atoms and from one to four heteroatoms independently selected from the group consisting of O, N, and S, wherein the nitrogen and sulfur heteroatoms can be optionally oxidized, the nitrogen can be optionally quaternized, and including any bicyclic group in which any of the above-defined heterocyclic rings is fused to a benzene ring, and wherein the heterocyclic ring can be substituted on carbon or on a nitrogen atom if the resulting compound is stable. Especially useful are rings containing one oxygen or sulfur, one to three nitrogen atoms, or one oxygen or sulfur combined with one or two nitrogen atoms. Examples of such heterocyclic groups include piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, and oxadiazolyl. Morpholino is the same as morpholinyl.

The term "heteroatom" is used herein to mean an oxygen atom ("O"), a sulfur atom ("S") or a nitrogen atom ("N"). It will be recognized that when the heteroatom is nitrogen, it may form an $NR^yR^z$ moiety, wherein $R^y$ and $R^z$ are, independently from one another, hydrogen or $C_1$ to $C_8$ alkyl, or together with the nitrogen to which they are bound, form a saturated or unsaturated 5-, 6-, or 7-membered ring.

The compounds of the present invention may be prepared by the general procedures outlined in Schemes I, II, and III where $R^1$–$R^6$, $R^{21}$–$R^{26}$, $R^a$, $R^b$, $R^c$, n, m, and j are as defined above. $P^a$ is an ester protecting group, such as ethyl or methyl; $P^b$, $P^c$, and $P^e$ are hydroxyl protecting groups, such as tert-butyldimethylsilyl and triisopropylsilyl; $P^d$ is an amino protecting group, such as tert-butoxycarbonyl (Boc) and benzyloxycarbonyl (Cbz). The schemes illustrate but are not limited to the preparation of the compounds of Examples 1 to 3.

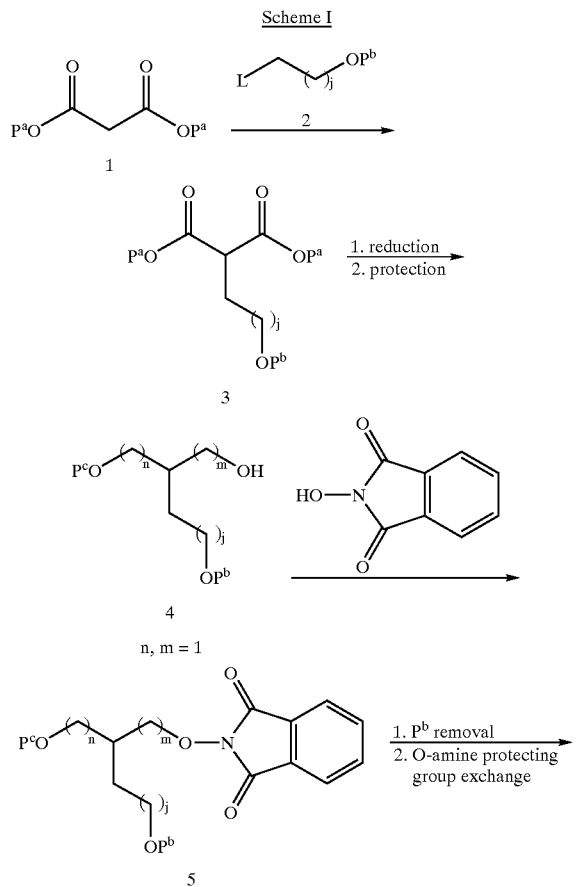

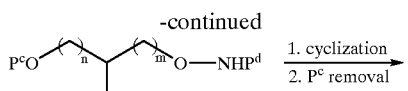

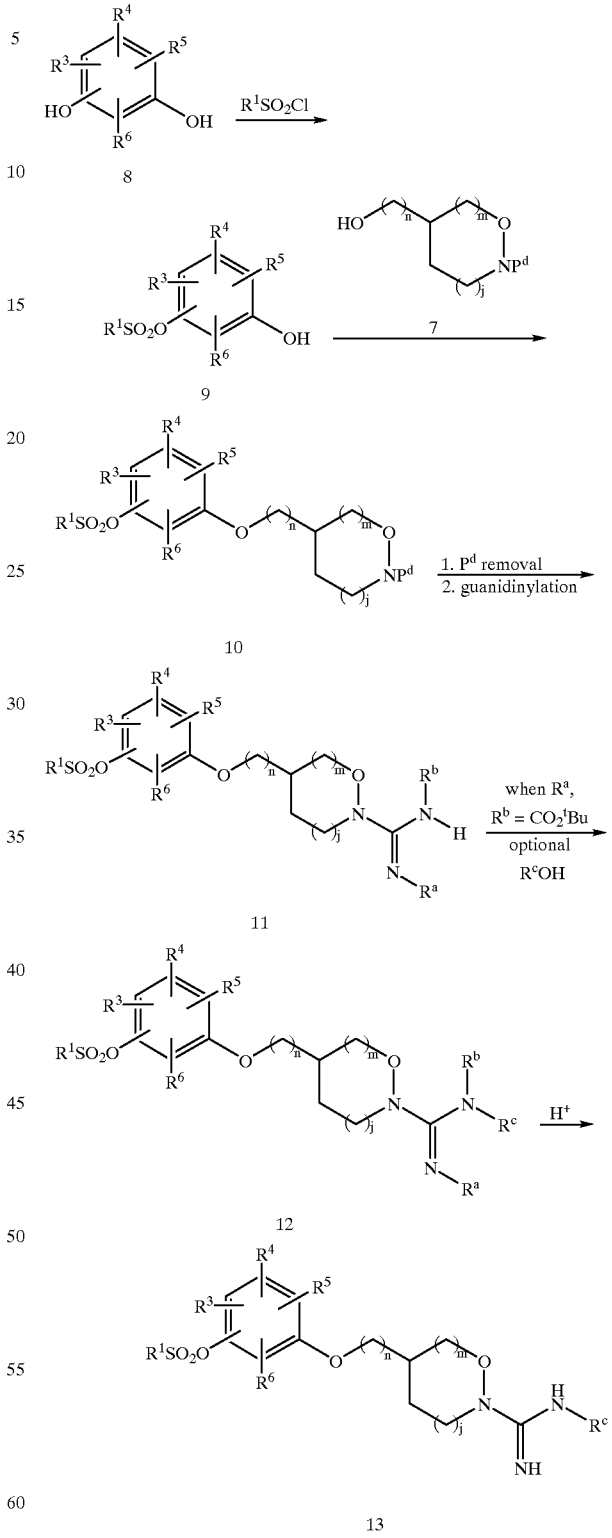

Scheme II

Scheme I outlines the synthetic steps to produce cyclic oxyamine 7, a precursor of cyclic oxyguanidine. Diethyl malonate 1 [$P^a$=ethyl] is deprotonated by treatment with a mild base, such as sodium ethoxide, to form an enolate in a polar protic solvent such as ethyl alcohol. This carbanion subsequently reacts with an alkylating reagent 2, where L is a reactive leaving group, such as a halide, to produce a monoalkylated compound 3. The ester groups of 3 are reduced with a reducing agent, such as lithium borohydride, in a suitable solvent, such as tetrahydrofuran, to give a diol (n, m=1). This symmetric diol is then monoprotected as a silyl ether by reacting with one equivalent of base such as sodium hydride in an appropriate solvent, such as tetrahydrofuran, followed by monosilylation with one equivalent of triisopropylsilyl chloride or other related reagents. Alcohol 4 is converted to 5 employing a Mitsunobu reaction with a N-hydroxycyclic imide derivative such as N-hydroxyphthalimide. Preferred reaction conditions include using a trialkylphosphine or triarylphosphine, such as tri-n-butylphosphine or triphenylphosphine, in a suitable solvent, such as tetrahydrofuran, and an azodicarbonyl reagent, such as diethyl azodicarboxylate or 1,1'-(azodicarbonyl)dipiperidine.

Selective deprotection of trialkylsilyl group $P^b$ ($P^b$=tert-butyldimethylsilyl) of 5 in the presence of another hydroxyl protecting group $P^c$ ($P^c$=triisopropylsilyl) is achieved by using an acid, such as fluorosilicic acid, in a suitable solvent system, such as 2-methyl-2-propanol and water. Unveiling of the phthalimide protecting group of 5 is accomplished using standard conditions well known in the art (Greene, T. W. and Wuts, P. G. M., *Protective Groups in Organic Synthesis*, $3^{rd}$ edition, John Wiley and Sons, Inc. New York (1999)), for example, using hydrazine or methylamine, or alternatively, sodium borohydride in a mixture of an appropriate alcohol (e.g., ethanol/water) followed by acidification. The released primary amine is then converted to carbamate 6, such as tert-butoxycarbamate, in a biphasic system composed of an organic solvent, such as dichloromethane, and a basic aqueous phase saturated with sodium bicarbonate. Intramolecular cyclization of 6 occurs to give a cyclic oxyamine under the standard Mitsunobu condition, i.e. using triphenylphosphine and diethyl azodicarboxylate in tetrahydrofuran. Deprotection of the hydroxyl protecting group $P^c$ is routinely accomplished using the conventional conditions. For example, triisopropylsilyl may be removed by reacting with tetrabutylammonium fluoride in tetrahydrofuran.

Scheme II outlines the synthetic steps to produce compounds of the present invention where Z of Formula I is $SO_2$, and Y=O. Phenol 8 is converted to monosulfonate 9 by reacting with appropriate sulfonyl chlorides. Preferred conditions include treating phenol 8 with a sulfonyl chloride in a biphasic system composed of an organic solvent, such as diethyl ether or dichloromethane, and an aqueous phase saturated with NaHCO₃. Alternatively, the conversion may be effected by first deprotonating 8 with one equivalent of a strong base, most preferably sodium hydride, in a polar solvent, such as N,N-dimethylformamide or tetrahydrofuran, followed by treating the phenoxyl anion with sulfonyl chlorides. Still alternatively, phenol 8 in a typical organic solvent, such as dichloromethane, may be converted to 9 by treating the phenol with sulfonyl chlorides in the presence of an amine base, such as 4-methylmorpholine.

Phenol 9 is coupled with 7 using a Mitsunobu procedure (Mitsunobu, O., *Synthesis* 1, (1981)), i.e. in the presence of triphenylphosphine and diethyl azodicarboxylate in tetrahydrofuran. Deprotection of the oxyamino protecting group $P^d$ of 10 is routinely accomplished using conventional conditions. For example, tert-butyloxycarbonyl (Boc) maybe removed in an acidic solution, such as trifluoroacetic acid in dichloromethane. Guanidinylation of the resulting cyclic O-amine may be achieved using standard reagents such as aminoiminosulfonic acid (Miller, A. E. and Bischoff, J. J., *Synthesis* 777 (1986)), or 1H-pyrazole-1-carboxamidine hydrochloride (Bernatowicz, M. S. et al., *J. Org. Chem.* 57(8):2497 (1992)), or substituted guanidinylating reagents such as N,N'-bis(tert-butoxycarbonyl)-S-methylisothiourea (Bergeron, R. J. and McManis, J. S., *J. Org. Chem.* 52:1700 (1987)) or N—$R^a$, N—$R^b$-1H-pyrazole-1-carboxamdine, where $R^a$ and $R^b$ are defined as above for Formula I. When $R^a$ and $R^b$ are protecting groups, for example t-butyloxycarbonyl (Boc), compound 11 can be optionally reacted with $R^c$OH using the standard Mitsunobu reaction condition as reviewed above to produce alkylated compound 12. These protecting groups can be optionally removed by treatment with acid, usually trifluoroacetic acid in a suitable solvent such as dichloromethane or water, or HCl gas dissolved in a suitable solvent, such as 1,4-dioxane to produce compound 13.

Scheme III

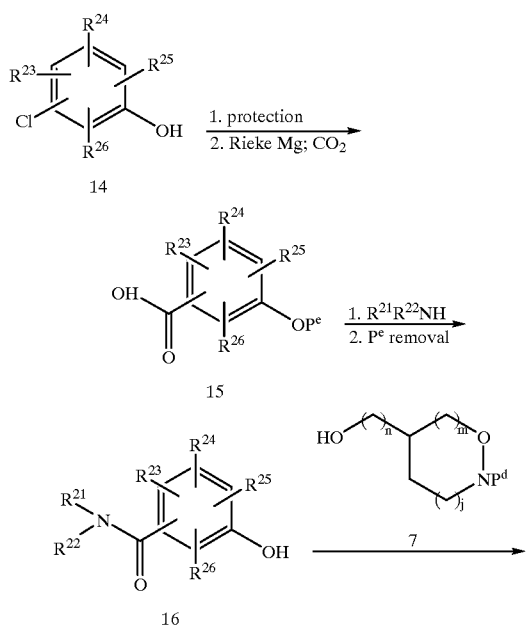

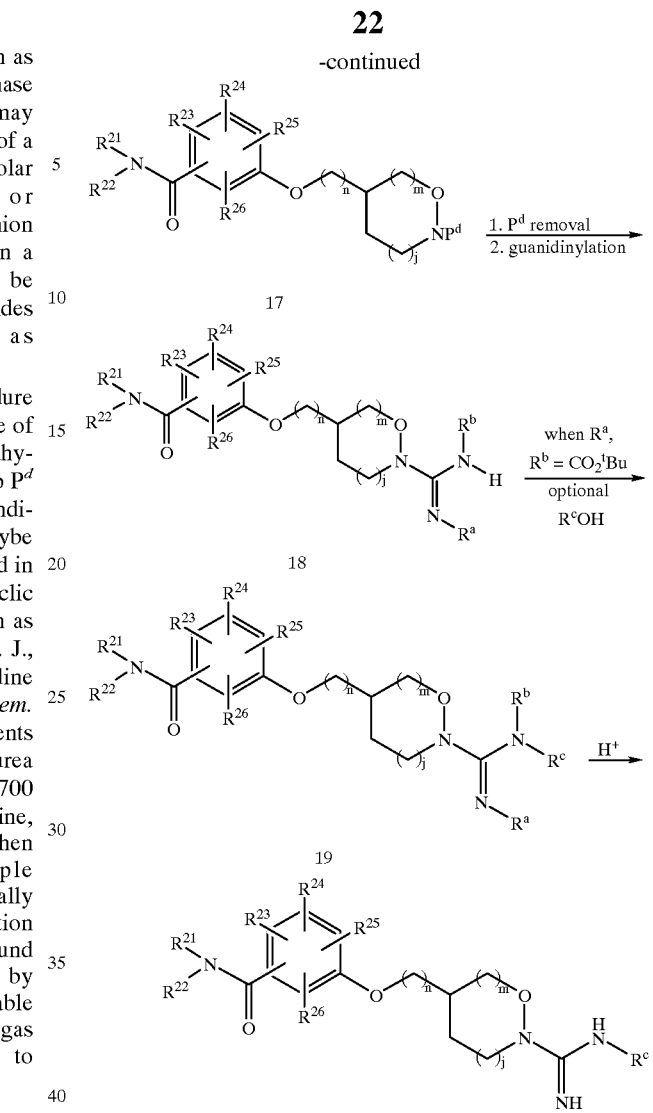

Scheme III outlines the synthetic step to produce compounds of the present invention where L of Formula II is C=O and Y=O. Thus, halogenated phenol 14 may be protected with a variety of protecting groups well known in the art, such as trialkylsilyl ethers, alkyl ethers, or esters (Greene, T. W., Wuts, P. G. M., *Protective Groups in Organic Synthesis*, 3rd edition, John Wiley and Sons, Inc. New York (1999)). The protected chloro-substituted compound is transformed to benzoic acid 15 by reacting with Rieke magnesium in a suitable solvent, such as diethyl ether or tetrahydrofuran, to form a Grignard intermediate which is then quenched with carbon dioxide. In the presence of a coupling reagent, such as 1,3-dicyclohexylcarbodiimide or Castro's reagent (BOP) (Castro, B., et al., *Tetrahedron Letter* 1219 (1975)), the benzoic acid 15 is reacted with amines to generate amides. The protecting group $P^e$ is removed under standard reaction conditions. When the protecting group $P^e$ is tert-butyldimethysilyl, the preferred condition involving using tetrabutylammonium fluoride in tetrahydrofuran to give phenol 16.

Phenol 16 is coupled with 7 using a Mitsunobu procedure (Mitsunobu, O., *Synthesis* 1, (1981)), i.e. in the presence of triphenylphosphine and diethyl azodicarboxylate in tetrahydrofuran. Deprotection of the oxyamino protecting group $P^d$ of 17 is routinely accomplished using conventional conditions. For example, tert-butyloxycarbonyl (Boc) may be removed in an acidic solution, such as trifluoroacetic acid in dichloromethane. Guanidinylation of the resulting cyclic O-amine may be achieved using standard reagents such as aminoiminosulfonic acid (Miller, A. E. and Bischoff, J. J., *Synthesis* 777 (1986)), or 1H-pyrazole-1-carboxamidine hydrochloride (Bernatowicz, M. S. et al., *J. Org. Chem.* 57(8):2497 (1992)), or substituted guanidinylating reagents such as N,N'-bis(tert-butoxycarbonyl)-S-methylisothiourea (Bergeron, R. J. and McManis, J. S., *J. Org. Chem.* 52:1700 (1987)) or N—$R^a$, N—$R^b$-1H-pyrazole-1-carboxamidine, where $R^a$ and $R^b$ are defined as above for Formula II. When $R^a$ and $R^b$ are protecting groups, for example t-butyloxycarbonyl (Boc), compound 18 can be optionally reacted with $R^cOH$ using the standard Mitsunobu reaction condition as reviewed above to produce alkylated compound 19. These protecting groups can be optionally removed by treatment with acid, usually trifluoroacetic acid in a suitable solvent such as dichloromethane or water, or HCl gas dissolved in a suitable solvent, such as 1,4-dioxane to produce compound 20.

The compounds of the present invention represent a novel class of potent inhibitors of metallo, acid, thiol and serine proteases. Examples of the serine proteases inhibited by compounds within the scope of the invention include leukocyte neutrophil elastase, a proteolytic enzyme implicated in the pathogenesis of emphysema; chymotrypsin and trypsin, digestive enzymes; pancreatic elastase, and cathepsin G, a chymotrypsin-like protease also associated with leukocytes; thrombin and factor Xa, proteolytic enzymes in the blood coagulation pathway. Inhibition of thermolysin, a metalloprotease, and pepsin, an acid protease, are also contemplated uses of compounds of the present invention. The compounds of the present invention are preferably employed to inhibit trypsin-like proteases.

An end use application of the compounds that inhibit chymotrypsin and trypsin is in the treatment of pancreatitis. For their end-use application, the potency and other biochemical parameters of the enzyme-inhibiting characteristics of the compounds of the present invention is readily ascertained by standard biochemical techniques well known in the art. Actual dose ranges for their specific end-use application will, of course, depend upon the nature and severity of the disease state of the patient or animal to be treated, as determined by the attending diagnostician. It is expected that a useful dose range will be about 0.01 to 10 mg per kg per day for an effective therapeutic effect.

Compounds of the present invention that are distinguished by their ability to inhibit either factor Xa or thrombin may be employed for a number of therapeutic purposes. As factor Xa or thrombin inhibitors, compounds of the present invention inhibit thrombin production. Therefore, these compounds are useful for the treatment or prophylaxis of states characterized by abnormal venous or arterial thrombosis involving either thrombin production or action. These states include, but are not limited to, deep vein thrombosis; disseminated intravascular coagulopathy which occurs during septic shock, viral infections and cancer; myocardial infarction; stroke; coronary artery bypass; fibrin formation in the eye; hip replacement; and thrombus formation resulting from either thrombolytic therapy or percutaneous transluminal coronary angioplasty (PCTA). Other uses include the use of said thrombin inhibitors as anticoagulants either embedded in or physically linked to materials used in the manufacture of devices used in blood collection, blood circulation, and blood storage, such as catheters, blood dialysis machines, blood collection syringes and tubes, blood lines and stents. The compounds of the present invention may also be used as an anticoagulant in extracorporeal blood circuits.

Metal stents have been shown to reduce restenosis, but are thrombogenic. A strategy for reducing the thrombogenicity of stents is to coat, embed, adsorb or covalently attach a thrombin-inhibiting agent to the stent surface. The compounds of the present invention can be employed for this purpose. Compounds of the invention can be attached to, or embedded within soluble and/or biodegradable polymers as and thereafter coated onto stent materials. Such polymers can include polyvinylpyrrolidone, polyhydroxy-propyl-methacrylamide-phenol, polyhydroxyethyl-aspartamide-phenol, or polyethyleneoxide-polylysine substituted with palmitoyl residues, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels. See European Application 761 251, European Application 604,022, Canadian Patent 2,164,684 and PCT Published Applications WO 96/11668, WO 96/32143 and WO 96/38136.

By virtue of the effects of both factor Xa and thrombin on a host of cell types, such as smooth muscle cells, endothelial cells and neutrophils, the compounds of the present invention find additional use in the treatment or prophylaxis of adult respiratory distress syndrome; inflammatory responses; wound healing; reperfusion damage; atherosclerosis; and restenosis following an injury such as balloon angioplasty, atherectomy, and arterial stent placement. The compounds of the present invention may be useful in treating neoplasia and metastasis as well as neurodegenerative diseases, such as Alzheimer's disease and Parkinson's disease.

When employed as thrombin or factor Xa inhibitors, the compounds of the present invention may be administered in an effective amount within the dosage range of about 0.1 to about 500 mg/kg, preferably between 0.1 to 10 mg/kg body weight, on a regimen in single or 2–4 divided daily doses.

When employed as inhibitors of thrombin, the compounds of the present invention may be used in combination with thrombolytic agents such as tissue plasminogen activator, streptokinase, and urokinase. Additionally, the compounds of the present invention may be used in combination with other antithrombotic or anticoagulant drugs such as, but not limited to, fibrinogen antagonists and thromboxane receptor antagonists.

Human leucocyte elastase is released by polymorphonuclear leukocytes at sites of inflammation and thus is a contributing cause for a number of disease states. Compounds of the present invention are expected to have an anti-inflammatory effect useful in the treatment of gout, rheumatoid arthritis and other inflammatory diseases, and in the treatment of emphysema. The leucocyte elastase inhibitory properties of compounds of the present invention are determined by the method described below. Cathepsin G has also been implicated in the disease states of arthritis, gout and emphysema, and in addition, glomerulonephritis and lung infestations caused by infections in the lung. In their end-use application the enzyme inhibitory properties of the compounds of Formulae I and II is readily ascertained by standard biochemical techniques that are well-known in the art.

The Cathepsin G inhibitory properties of compounds within the scope of the present invention are determined by the following method. A preparation of partially purified human Cathepsin G is obtained by the procedure of Baugh et al., *Biochemistry* 15: 836 (1979). Leukocyte granules are a major source for the preparation of leukocyte elastase and cathepsin G (chymotrypsin-like activity). Leukocytes are lysed and granules are isolated. The leukocyte granules are extracted with 0.20 M sodium acetate, pH 4.0, and extracts are dialyzed against 0.05 M Tris buffer, pH 8.0 containing 0.05 M NaCl overnight at 4° C. A protein fraction precipitates during dialysis and is isolated by centrifugation. This fraction contains most of the chymotrypsin-like activity of leukocyte granules. Specific substrates are prepared for each enzyme, namely N-Suc-Ala-Ala-Pro-Val-p-nitroanilide and Suc-Ala-Ala-Pro-Phe-p-nitroanilide. The latter is not hydrolyzed by leukocyte elastase. Enzyme preparations are assayed in 2.00 mL of 0.10 M Hepes buffer, pH 7.5, containing 0.50 M NaCl, 10% dimethylsulfoxide and 0.0020 M Suc-Ala-Ala-Pro-Phe-p-nitroanilide as a substrate. Hydrolysis of the p-nitroanilide substrate is monitored at 405 nm and at 25° C.

Useful dose range for the application of compounds of the present invention as neutrophil elastase inhibitors and as Cathepsin G inhibitors depend upon the nature and severity of the disease state, as determined by the attending diagnostician, with a range of 0.01 to 10 mg/kg body weight, per day, being useful for the aforementioned disease states.

Compounds of the present invention that inhibit urokinase or plasminogen activator are potentially useful in treating excessive cell growth disease state. As such compounds of the present invention may also be useful in the treatment of benign prostatic hypertrophy and prostatic carcinoma, the treatment of psoriasis, and as abortifacients. For their end-use application, the potency and other biochemical parameters of the enzyme inhibiting characteristics of compounds of the present invention are readily ascertained by standard biochemical techniques well known in the art. Actual dose ranges for this application will depend upon the nature and severity of the disease state of the patient or animal to be treated as determined by the attending diagnostician. It is to be expected that a general dose range will be about 0.01 to 10 mg per kg per day for an effective therapeutic effect.

Additional uses for compounds of the present invention include analysis of commercial reagent enzymes for active site concentration. For example, chymotrypsin is supplied as a standard reagent for use in clinical quantitation of chymotrypsin activity in pancreatic juices and feces. Such assays are diagnostic for gastrointestinal and pancreatic disorders. Pancreatic elastase is also supplied commercially as a reagent for quantitation of $\alpha_1$-antitrypsin in plasma. Plasma $\alpha_1$-antitrypsin increases in concentration during the course of several inflammatory diseases, and $\alpha_1$-antitrypsin deficiencies are associated with increased incidence of lung disease. Compounds of the present invention can be used to enhance the accuracy and reproducibility of these assays by titrametric standardization of the commercial elastase supplied as a reagent. See, U.S. Pat. No. 4,499,082.

Protease activity in certain protein extracts during purification of particular proteins is a recurring problem which can complicate and compromise the results of protein isolation procedures. Certain proteases present in such extracts can be inhibited during purification steps by compounds of the present invention, which bind tightly to various proteolytic enzymes.

The pharmaceutical compositions of the invention can be administered to any animal that can experience the beneficial effects of the compounds of the invention. Foremost among such animals are humans, although the invention is not intended to be so limited.

The pharmaceutical compositions of the present invention can be administered by any means that achieve their intended purpose. For example, administration can be by parenteral, subcutaneous, intravenous, intramuscular, intraperitoneal, transdermal, buccal, or ocular routes. Alternatively, or concurrently, administration can be by the oral route. The dosage administered will be dependent upon the age, health, and weight of the recipient, kind of concurrent treatment, if any, frequency of treatment, and the nature of the effect desired.

In addition to the pharmacologically active compounds, the new pharmaceutical preparations can contain suitable pharmaceutically acceptable carriers comprising excipients and auxiliaries that facilitate processing of the active compounds into preparations that can be used pharmaceutically.

The pharmaceutical preparations of the present invention are manufactured in a manner that is, itself, known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example, lactose or sucrose, mannitol or sorbitol, cellulose preparations and/or calcium phosphates, for example, tricalcium phosphate or calcium hydrogen phosphate, as well as binders, such as, starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents can be added, such as, the above-mentioned starches and also carboxymethyl-starch, cross-linked polyvinyl pyrrolidone, agar, or alginic acid or a salt thereof, such as, sodium alginate. Auxiliaries are, above all, flow-regulating agents and lubricants, for example, silica, talc, stearic acid or salts thereof, such as, magnesium stearate or calcium stearate, and/or polyethylene glycol. Dragee cores are provided with suitable coatings that, if desired, are resistant to gastric juices. For this purpose, concentrated saccharide solutions can be used, which may optionally contain gum arabic, talc, polyvinyl pyrrolidone, polyethylene glycol, and/or titanium dioxide, lacquer solutions and suitable organic solvents or solvent mixtures. In order to produce coatings resistant to gastric juices, solutions of suitable cellulose preparations, such as, acetylcellulose phthalate or hydroxypropylmethyl-cellulose phthalate, are used. Dye stuffs or pigments can be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer, such as, glycerol or sorbitol. The push-fit capsules can contain the active compounds in the form of granules that may be mixed with fillers such as lactose, binders such as starches, and/or lubricants such as talc or magnesium stearate and, optionally, stabilizers. In soft capsules, the active compounds are preferably dissolved or suspended in suitable liquids, such as, fatty oils or liquid paraffin. In addition, stabilizers may be added.

Suitable formulations for parenteral administration include aqueous solutions of the active compounds in water-soluble form, for example, water-soluble salts, alkaline solutions and cyclodextrin inclusion complexes. Especially preferred salts are hydrochloride and acetate salts. One or more modified or unmodified cyclodextrins can be employed to stabilize and increase the water solubility of compounds of the present invention. Useful cyclodextrins for this purpose are disclosed in U.S. Pat. Nos. 4,727,064, 4,764,604, and 5,024,998.

In addition, suspensions of the active compounds as appropriate oily injection suspensions can be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions can contain substances that increase the viscosity of the suspension, for example, sodium carboxymethyl cellulose, sorbitol, and/or dextran. Optionally, the suspension may also contain stabilizers.

The following examples are illustrative, but not limiting, of the method and compositions of the present invention. Other suitable modifications and adaptations of the variety of conditions and parameters normally encountered and obvious to those skilled in the art are within the spirit and scope of the invention.

EXAMPLE 1

3-[(2-Amidino(1,2-oxazaperhydroin-5-yl))methoxy]-5-methylphenyl 2-(methylsulfonyl)benzenesulfonate Trifluoroacetate

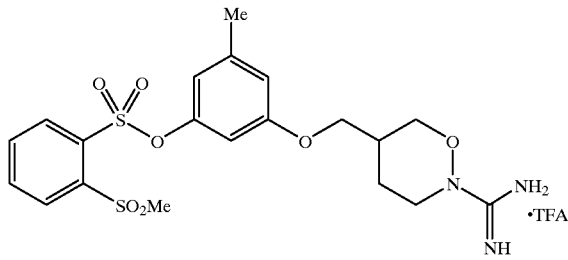

1. Diethyl 2-[2-(1,1,2,2-tetramethyl-1-silapropoxy)ethyl]propane-1,3-dioate

A solution of diethyl malonate (5.14 g, 32.1 mmol) in anhydrous ethyl alcohol (100 mL) was reacted with 96% sodium ethoxide (2.28 g, 32.2 mmol) at 76° C. for 1 h. After the solution cooled to room temperature, (2-bromoethoxy)-tert-butyldimethylsilane (7.68 g, 32.1 mmol) was added. The resulting solution was heated at 76° C. for 15.5 h and then concentrated. The residue was partitioned between dichloromethane and water. The organic layer was dried ($Na_2SO_4$) and concentrated to give the title compound as a brown oil (10.22 g, 100%). $^1$H NMR ($CDCl_3$) δ 4.19–4.11 (m, 4H), 3.62 (t, 2H, J=6.0 Hz), 3.55 (t, 1H, J=7.3 Hz), 2.10–2.06 (m, 2H), 1.23 (t, 6H, J=7.1 Hz), 0.85 (s, 9H), 0.01 (s, 6H).

2. 2-[2-(1,1,2,2-Tetramethyl-1-silapropoxy)ethyl]propane-1,3-diol

To a solution of the product (10.22 g, 32.1 mmol) of the preceding step in tetrahydrofuran (150 mL) was slowly added 2.0 M lithium borohydride (33 mL, 66 mmol) in tetrahydrofuran at room temperature. After 2.5 h, the reaction was quenched with water dropwise at 4° C., and a white solid formed. The precipitate was filtered, the filtrate was washed with brine, and the aqueous solution was back extracted with dichloromethane. The combined organic phases were dried, concentrated, and flash chromatographed to provide the title compound as a clear oil (4.13 g, 55.0%). $^1$H NMR ($CDCl_3$) δ 3.76–3.70 (m, 6H), 2.74 (m, 2H), 1.89–1.84 (m, 1H), 1.67–1.62 (m, 2H), 0.91 (s, 9H), 0.08 (s, 6H).

3. 2-{[1,1-Bis(methylethyl)-2-methyl-1-silapropoxy]methyl}-4-(1,1,2,2-tetramethyl-1-silapropoxy)butan-1-ol To a solution of the product (4.13 g, 17.6 mmol) of the preceding step in tetrahydrofuran (40 mL) was added 60% NaH (0.78 g, 19.5 mmol) in mineral oil at 4° C. After completion of the addition, the cooling bath was removed and the solution was allowed to warm up to room temperature for 1 h. Triisopropylsilyl chloride (3.51 g, 18.2 mmol) was then added. After 3 h, brine was added, the organic phase was separated, and the aqueous layer was extracted with dichloromethane. The combined organic layers were dried, concentrated, and flash chromatographed to provide the title compound as a clear oil (4.16 g, 60.4%). $^1$H NMR ($CDCl_3$) δ 3.83 (dd, 1H, J=4.9, 9.8 Hz), 3.76–3.65 (m, 5H), 1.95–1.90 (m, 1H), 1.57–1.51 (m, 2H), 1.10–1.04 (m, 3H), 1.06 (d, 18H, J=6.6 Hz), 0.90 (s, 9H), 0.06 (s, 6H).

4. 2-(2-{[1,1-Bis(methylethyl)-2-methyl-1-silapropoxy]methyl}-4-(1,1,2,2-tetramethyl-1-silapropoxy)butoxy)isoindoline-1,3-dione To a solution of the product (4.16 g, 10.7 mmol) of the preceding step, triphenylphosphine (3.35 g, 12.8 mmol), N-hydroxyphthalimide (1.91 g, 11.7 mmol), and tetrahydrofuran (40 mL) was slowly added diethyl azodicarboxylate (2.0 mL, 12.7 mmol) at room temperature. After overnight, the solvent was removed in vacuo and the residue was flash chromatographed to give the title compound as a yellow oil (5.28 g, 92.5%). $^1$H NMR ($CDCl_3$) δ 7.84–7.82 (m, 2H), 7.75–7.72 (m, 2H), 4.34–4.29 (m, 1H), 4.19 (dd, 1H, J=5.4, 9.1 Hz), 3.96 (dd, 1H, J=4.6, 9.9 Hz), 3.81 (dd, 1H, J=5.4, 9.9 Hz), 3.75 (t, 2H, J=6.4 Hz), 2.17–2.13 (m, 1H), 1.93–1.83 (m, 2H), 1.07–1.03 (m, 21H), 0.85 (s, 9H), 0.04 (s, 6H).

5. 2-(2-{[1,1-Bis(methylethyl)-2-methyl-1-silapropoxy]methyl}-4-hydroxybutoxy)isoindoline-1,3-dione To a plastic bottle containing the product (4.10 g, 7.66 mmol) of the preceding step and tert-butyl alcohol (60 mL) was added 20–25% wt. fluorosilicic acid (3.8 mL, 6.4–8.0 mmol) in water. After stirring for 3 h at room temperature, the solution was basified with saturated sodium bicarbonate and concentrated under reduced pressure. Dichloromethane and water were added and the mixture was filtered. The filtrate was separated and the aqueous layer was extracted with dichloromethane. The combined organic layers were dried, concentrated, and flash chromatographed to obtain the title compound as a clear oil (2.12 g, 65.7%). $^1$H NMR ($CDCl_3$) δ 7.85–7.82 (m, 2H), 7.78–7.74 (m, 2H), 4.33–4.29 (m, 1H), 4.20 (dd, 1H, J=6.3, 9.4 Hz), 3.90–3.82 (m, 4H), 2.67 (s(br), 1H), 2.23–2.18 (m, 1H), 1.89–1.75 (m, 2H).

6. (tert-Butoxy)-N-(2-{[1,1-bis(methylethyl)-2-methyl-1-silapropoxy]methyl}-4-hydroxybutoxy)carboxamide A solution of the product (2.57 g, 6.10 mmol), as prepared in the preceding step, in methanol (20 mL) was treated with 40% wt. methylamine (1.90 g, 24.5 mmol) in water for 30 min. After the solvent was removed in vacuo, the residue was diluted with ethyl acetate, a white solid was filtered, and the filtrate was concentrated to yield an oil. To the oil in dichloromethane (20 mL) and water (10 mL) was added sodium bicarbonate (1.54 g, 18.3 mmol) and di-tert-butyl dicarbonate (2.00 g, 9.17 mmol). After stirring overnight, the organic phase was separated and the aqueous phase was extracted with dichloromethane. The combined organic layers were dried, concentrated, and flash chromatographed to provide the title compound as a clear oil (1.90 g, 79.6%). $^1$H NMR ($CDCl_3$) δ 7.23 (s(br), 1H), 3.99–3.92 (m, 1H), 3.88–3.82 (m, 1H), 3.78–3.66 (m, 4H), 2.99–2.94 (m, 1H), 2.12–2.04 (m, 1H), 1.74–1.68 (m, 2H), 1.48 (s, 9H), 1.14–1.03 (m, 21H).

7. tert-Butyl 5-{[1,1-bis(methylethyl)-2-methyl-1-silapropoxy]methyl}-1,2-oxazaperhydroine-2-carboxylate To a solution of the product (1.88 g, 4.81 mmol), as prepared in the preceding step, in tetrahydrofuran (30 mL) was added triphenylphosphine (1.89 g, 7.21 mmol) and diethyl azodicarboxylate (1.2 mL, 7.6 mmol). After 2 h at room temperature, the solution was concentrated and flash chromatographed to give the title compound as an orange oil (1.45 g, 80.8%). $^1$H NMR (CDCl$_3$) δ 4.12 (dd, 1H, J=4.1, 11.3 Hz), 3.97 (dt, 1H, J=4.0, 13.5 Hz), 3.71 (dd, 1H, J=9.9, 11.4 Hz), 3.65 (dd, 1H, J=5.3, 10.0 Hz), 3.57 (dd, 1H, J=7.0, 10.0 Hz), 3.33 (m, 1H), 2.11–2.03 (m, 1H), 1.72–1.65 (m, 2H), 1.50 (s, 9H), 1.09–1.03 (m, 21H).

8. tert-Butyl 5-(hydroxymethyl)-1,2-oxazaperhydroine-2-carboxylate

A solution of the product (632 mg, 1.69 mmol) of the preceding step in tetrahydrofuran (30 mL) was treated with 1.0 M tetrabutylammonium fluoride (2.0 mL, 2.0 mmol) in tetrahydrofuran. After 2 h, the solution was concentrated, and the residue was partitioned between dichloromethane and water. The organic phase was dried, concentrated, and flash chromatographed to obtain the title compound as a clear oil (328 mg, 89.2%). $^1$H NMR (CDCl$_3$) δ 4.13 (dd, 1H, J=4.3, 11.7 Hz), 3.95 (dt, 1H, J=4.3, 13.5 Hz), 3.69 (dd, 1H, J=9.5, 11.5 Hz), 3.63–3.53 (m, 2H), 3.36 (m, 1H), 2.11–2.04 (m, 1H), 1.81–1.66 (m, 2H). Mass spectrum (LCMS, ESI) calcd. for C$_{10}$H$_{19}$NO$_4$: 240 (M+Na). Found: 240.

9. 3-Hydroxy-5-methylphenyl 2-(methylsulfonyl)benzenesulfonate

To a stirred solution of 2-methylsulfonylbenzenesulphonyl chloride (3.63 g, 14.2 mmol) and orcinol monohydrate (2.02 g, 14.2 mmol) in dichloromethane (50 mL) was added saturated NaHCO$_3$ aqueous solution (30 mL) dropwise in 30 min. After stirred vigorously at room temperature for 3 days, water was added. The organic layer was separated and the aqueous layer was extracted with dichloromethane. The combined organic phases were dried over Na$_2$SO$_4$, filtered, and concentrated to half of the volume (~60 mL). Hexanes (30–40 mL) were added to initiate crystallization. After standing overnight, the mixture was filtered, and the solid was rinsed with small amount of diethyl ether and dichloromethane to give the title compound as a pale pink solid (2.18 g, 44.8%). $^1$H NMR (CDCl$_3$) δ 8.43 (dd, 1H, J=1.3, 7.9 Hz), 8.11 (dd, 1H, J=1.3, 7.9 Hz), 7.87 (td, 1H, J=1.4, 7.7 Hz), 7.73 (td, 1H, J=1.4, 7.7 Hz), 6.58 (s, 1H), 6.55 (s, 1H), 6.51 (s, 1H), 3.45 (s, 3H), 2.21 (s, 3H).

10. 5-Methyl-3-(1,2-oxazaperhydroin-5-ylmethoxy)phenyl 2-(methylsulfonyl)benzenesulfonate To a solution of 3-hydroxy-5-methylphenyl 2-(methylsulfonyl)benzenesulfonate (660 mg, 1.93 mmol), as prepared in the preceding step, and tert-butyl 5-(hydroxymethyl)-1,2-oxazaperhydroine-2-carboxylate (350 mg, 1.61 mmol), the product of step 8 of Example 1, in tetrahydrofuran (15 mL) were added triphenylphosphine (550 mg, 2.10 mmol) and diethyl azodicarboxylate (0.33 mL, 2.10 mmol) at room temperature. After stirring overnight, the reaction solution was concentrated and flash chromatographed (SiO$_2$) to give a white solid. The solid in dichloromethane (10 mL) was treated with trifluoroacetic acid (3 mL) for 1 h at room temperature. The solution was concentrated, and the residue was partitioned between dichloromethane and saturated sodium bicarbonate. The organic layer was dried, concentrated, and flash chromatographed to give the title compound as white foam (441 mg, 62.0%). $^1$H NMR (CDCl$_3$) δ 8.45 (dd, 1H, J=1.2, 7.8 Hz), 8.13 (dd, 1H, J=1.2, 7.8 Hz), 7.88 (td, 1H, J=1.3, 7.7 Hz), 7.75 (td, 1H, J=1.3, 7.8 Hz), 6.61–6.56 (m, 3H), 4.15–4.10 (m, 1H), 3.79–3.71 (m, 2H), 3.61 (dd, 1H, J=9.2, 11.5 Hz), 3.45 (s, 3H), 3.19–3.16 (m, 2H), 2.24 (s, 3H), 2.24–2.19 (m, 1H), 1.90–1.86 (m, 1H), 1.58–1.54 (m, 1H). Mass spectrum (LCMS, ESI) calcd. for C$_{19}$H$_{23}$NO7S$_2$: 442 (M+H). Found: 442.

11. tert-Butyl-2-aza-3-[(tert-butoxy)carbonylamino]-3-{5-[(5-methyl-3-{[2-(methylsulfonyl)phenyl]sulfonyloxy}phenoxy)methyl](1,2-oxazaperhydroin-2-yl)}prop-2-enoate To a solution of the product (441 mg, 1.00 mmol) of the preceding step in N,N-dimethylformamide (8 mL) was added N',N-bis(tert-butoxycarbonyl)-1H-pyrazole-1-carboxamidine (372 mg, 1.20 mmol). After stirring overnight at room temperature, the solvent was evaporated and the residue was flash chromatographed to yield the title compound as white foam (592 mg, 86.7%). $^1$H NMR (CDCl$_3$) δ 9.02 (s(br), 1H), 8.45 (dd, 1H, J=1.1, 7.8 Hz), 8.13 (dd, 1H, J=1.0, 7.8 Hz), 7.89 (td, 1H, J=1.2, 7.7 Hz), 7.75 (td, 1H, J=1.2, 7.7 Hz), 6.63 (s, 1H), 6.58 (s, 1H), 6.56 (s, 1H), 4.23–4.19 (m, 2H), 3.89 (dd, 1H, J=9.4, 11.3 Hz), 3.80 (m, 1H), 3.75–3.71 (m, 1H), 3.45 (s, 3H), 3.45–3.39 (m, 1H), 2.33–2.28 (m, 1H), 2.24 (s, 3H), 1.92–1.87 (m, 1H), 1.71–1.61 (m, 1H), 1.50 (m, 18H).

12. 3-[(2-Amidino(1,2-oxazaperhydroin-5-yl))methoxy]-5-methylphenyl 2-(methylsulfonyl)benzenesulfonate trifluoroacetate The product (592 mg, 0.867 mmol) of the preceding step in dichloromethane (6 mL) was treated with trifluoroacetic acid (2 mL) for 2 h. The solution was concentrated, methanol and hexane were added, and the solution was concentrated in vacuo again to obtain the title compound as a white solid (519 mg, 100%). $^1$H NMR (DMSO-d6) δ 8.37 (dd, 1H, J=1.2, 7.8 Hz), 8.14–8.08 (m, 2H), 7.96 (td, 1H, J=1.2, 7.7 Hz), 7.73 (s(br), 3H), 6.77 (s, 1H), 6.54–6.53 (m, 2H), 4.17 (dd, 1H, J=4.1, 11.3 Hz), 4.07–4.03 (m, 1H), 3.89 (dd, 2H, J=6.5 Hz), 3.78 (dd, 1H, J=9.4, 11.4 Hz), 3.57–3.51 (m, 1H), 3.47 (s, 3H), 2.32–2.29 (m, 1H), 2.22 (s, 3H), 1.90–1.86 (m, 1H), 1.59–1.56 (m, 1H). Mass spectrum (LCMS, ESI) calcd. for C$_{20}$H$_{25}$N$_3$O$_7$S$_2$: 484 (M+H). Found: 484.

EXAMPLE 2

3-[(2-Amidino(1,2-oxazaperhydroin-5-yl))methoxy]-5-chlorophenyl 2-(methylsulfonyl)benzenesulfonate trifluoroacetate

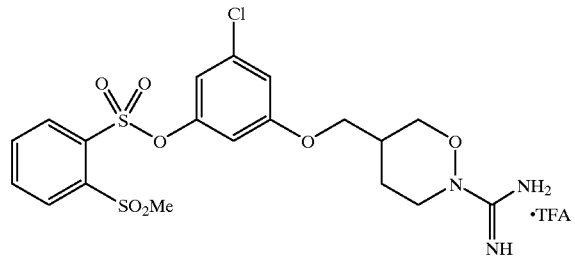

1. 5-Chloro-3-(1,2-oxazaperhydroin-5-ylmethoxy)phenyl 2-(methylsulfonyl)benzenesulfonate To a solution of 5-chloro-3-[(2-methylsulfonyl) phenylsulfonyloxy]phenol (245 mg, 0.676 mmol) and tert-butyl 5-(hydroxymethyl)-1,2-oxazaperhydroine-2-carboxylate (149 mg, 0.687 mmol), the product of step 8 of Example 1, in tetrahydrofuran (15 mL) were added triphenylphosphine (212 mg, 0.809 mmol) and diethyl azodicarboxylate (150 mg, 0.862 mmol) at room temperature. After stirring overnight, the reaction solution was concentrated and flash chromatographed (SiO$_2$) to give a white solid. This solid in dichloromethane (8 mL) was treated with trifluoroacetic acid (4 mL) for 3 h at room temperature. The solution was concentrated, and the residue was partitioned between dichloromethane and saturated sodium bicarbonate. The organic layer was dried, concentrated, and flash chromatographed to give the title compound as a clear oil (158 mg, 50.0%). $^1$H NMR (CDCl$_3$) δ 8.47 (dd, 1H, J=1.3, 7.8 Hz), 8.17 (dd, 1H, J=1.3, 7.9 Hz), 7.92 (td, 1H, J=1.3, 7.7 Hz), 7.79 (td, 1H, J=1.3, 7.7 Hz), 6.86 (t, 1H, J=1.9 Hz), 6.79 (t, 1H, J=2.0 Hz), 6.71 (t, 1H, J=2.2 Hz), 4.13–4.09 (m, 1H), 3.82–3.75 (m, 2H), 3.62 (dd, 1H, J=9.1, 11.6 Hz), 3.45 (s, 3H), 3.19–3.16 (m, 2H), 2.24–2.19 (m, 1H), 1.91–1.87 (m, 2H), 1.62–1.54 (m, 1H).

2. tert-Butyl-2-aza-3-[(tert-butoxy)carbonylamino]-3-{5-[(5-chloro-3-{[2-(methylsulfonyl)phenyl] sulfonyloxy}phenoxy)methyl](1,2-oxazaperhydroin-2-yl)}prop-2-enoate To a solution of the product (145 mg, 0.314 mmol) of the preceding step in N,N-dimethylformamide (5 mL) was added N,N'-bis(tert-butoxycarbonyl)-1H-pyrazole-1-carboxamidine (117 mg, 0.377 mmol). After stirring at 42° C. overnight, the solvent was evaporated and the residue was flash chromatographed to yield the title compound as a clear oil (94 mg, 43%). $^1$H NMR (CDCl$_3$) δ 8.46 (dd, 1H, J=1.2, 7.8 Hz), 8.17 (dd, 1H, J=1.3, 7.8 Hz), 7.93 (td, 1H, J=1.3, 7.7 Hz), 7.80 (td, 1H, J=1.3, 7.7 Hz), 7.62 (m, 1H), 6.87 (t, 1H, J=1.9 Hz), 6.79 (t, 1H, J=2.0 Hz), 6.71 (t, 1H, J=2.1 Hz), 4.23–4.16 (m, 2H), 3.90 (dd, 1H, J=9.2, 11.4 Hz), 3.85–3.75 (m, 2H), 3.44 (s, 3H), 2.33–2.30 (m, 1H), 1.93–1.89 (m, 1H), 1.71–1.64 (m, 1H), 1.50 (s, 18H).

3. 3-[(2-Amidino(1,2-oxazaperhydroin-5-yl))methoxy]-5-chlorophenyl 2-(methylsulfonyl)benzenesulfonate trifluoroacetate The product (94 mg, 0.134 mmol) of the preceding step in dichloromethane (2 mL) was treated with trifluoroacetic acid (1 mL) for 0.5 h. The solution was concentrated and the residue was purified on Waters' sep-pak (SiO$_2$, 5 g) to obtain the title compound as a white solid (70 mg, 85%). $^1$H NMR (DMSO-d$_6$) δ 8.38 (dd, 1H, J=1.0, 7.9 Hz), 8.18 (dd, 1H, J=1.0, 7.9 Hz), 8.13 (td, 1H, J=1.0, 7.7 Hz), 7.99 (td, 1H, J=1.1, 7.7 Hz), 7.78 (s, 4H), 7.11 (t, 1 H, J=1.9 Hz), 6.82 (t, 1H, J=1.8 Hz), 6.76 (t, 1H, J=2.1 Hz), 4.17 (dd, 1H, J=3.8, 11.4 Hz), 4.07–4.01 (m, 1H), 3.98 (d, 2H, J=6.6 Hz), 3.78 (dd, 2H. J=9.2, 11.4 Hz), 3.58–3.51 (m, 1H), 3.48 (s, 3H), 2.35–2.30 (m, 1H), 1.90–1.86 (m, 1H), 1.61–1.55 (m, 1H). Mass spectrum (LCMS, ESI) calcd. for C$_{19}$H$_{22}$ClN$_3$O$_7$S$_2$: 504.5 (M+H). Found: 504.5.

EXAMPLE 3

5-{[5-Chloro-3-(N-cyclopentyl-N-prop-2-enylcarbamoyl)phenoxy]methyl}-1,2-oxazaperhydroine-2-carboxamidine trifluoroacetate

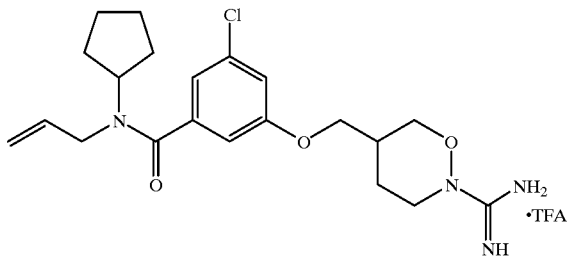

1. 1,3-Dichloro-5-(tert-butyldimethylsilyloxy)benzene

To a solution of 3,5-dichlorophenol (5.0 g, 30 mmol) and CH$_2$Cl$_2$ (60 mL) were added tert-butyldimethylsilyl chloride (5.54 g, 36 mmol), N,N-diisopropylethylamine (8.0 mL, 46 mmol), and a catalytic amount of 4-dimethylaminopyridine. The initially exothermic solution was stirred at ambient temperature for 6 h then diluted with CH$_2$Cl$_2$ (40 mL). The mixture was washed consecutively with 10% aqueous HCl (50 mL), saturated aqueous NaHCO$_3$ (50 mL), and brine (50 mL). The organic phase was dried over anhydrous MgSO$_4$, filtered, and concentrated in vacuo to provide the title compound as a pale yellow liquid (8.8 g, 100%). $^1$H NMR (CDCl$_3$) δ 6.98 (s, 1H), 6.72 (s, 2H), 0.98 (s, 9H), 0.22 (s, 6H).

2. 3-Chloro-5-(tert-butyldimethylsilyloxy)benzoic Acid

To "Rieke Mg" (0.21 mol; Rieke et al., *Org. Synth. Collective Volume VI*:845 (1988)) in tetrahydrofuran (1000 mL) was added 1,3-dichloro-5-(tert-butyldimethylsilyloxy) benzene (27.7 g, 0.10 mol), as prepared in the preceding step. After the reaction mixture was stirred for 20 min at ambient temperature, there was an exotherm observed. The exotherm subsided within 5 min, and the reaction mixture was cooled to 20° C. with an ice bath. After 15 min, the reaction mixture was cooled to −78° C. To the cool reaction mixture was bubbled with CO$_2$ gas for 30 min. The reaction mixture was warmed to ambient temperature, then diluted with cold (0° C.) 10% aqueous HCl (150 mL) and ethyl acetate (400 mL). The organic phase was separated and the aqueous phase was extracted with ethyl acetate (400 mL). The combined organic phases were washed with brine, dried over anhydrous MgSO$_4$, filtered, and concentrated in vacuo. The resulting solid was recrystallized from acetonitrile to provide the title compound as fluffy white needles (19.3 g, 64%). $^1$H NMR (CDCl$_3$) δ 7.70 (s, 1H), 7.43 (s, 1H), 7.08 (s, 1H), 0.99 (s, 9H), 0.23 (s, 6H). IR (KBr) 2957, 1697, 1578, 1434, 1297, 1266, 1115, 990, 871 cm$^{-1}$.

3. [3-Chloro-5-(tert-butyldimethylsilyloxy)phenyl]-N-cyclopentyl-N-prop-2-enylcarboxamide To a solution of 3-chloro-5-(tert-butyldimethylsilyloxy) benzoic acid (17.5 g, 60 mmol), as prepared in the preceding step, and CH$_2$Cl$_2$ (250 mL) were added triethylamine (33.8 mL, 0.24 mol) and bis(2-oxo-3-oxazolidinyl)phosphinic chloride (17.0 g, 66 mmol). The resulting mixture was stirred for 5 min, then N-allylcyclopentylamine (9.8 mL, 66 mmol) was added. After 1 h, the solution was filtered. The filtrate was washed with 10% aqueous HCl (100 mL), saturated aqueous NaHCO$_3$ (100 mL), and brine (100 mL). The organic layer was dried over anhydrous MgSO$_4$, concentrated in vacuo, and flash chromatographed to provide the title compound as a colorless oil (23.5 g, 97%). $^1$H NMR (CDCl$_3$) δ 6.95 (s, 1H), 6.84 (s, 1H), 6.71 (s, 1H), 5.93 (br s, 1H), 5.16 (d, 2H), 3.95 (br s, 3H), 1.4–1.9 (m, 8H), 0.97 (s, 9H), 0.20 (s, 6H). Mass spectrum (CI) calcd. for C$_{21}$H$_{32}$NO$_2$SiCl: 394 (M+H). Found: 394.

4. (5-Chloro-3-hydroxyphenyl)-N-cyclopentyl-N-prop-2-enylcarboxamide

To a solution of the product (23.4 g, 59 mmol) of the preceding step and tetrahydrofuran (200 mL) was added 1.0 M tetrabutylammonium fluoride (66 mL, 66 mmol) in tetrahydrofuran. The solution was stirred for 30 min, then poured into a separation funnel containing 10% aqueous HCl (100 mL) and ethyl acetate (200 mL). The organic layer was separated and the aqueous layer was extracted with ethyl acetate (200 mL). The organic layers were combined, washed with brine (100 mL), dried over anhydrous MgSO$_4$, and concentrated in vacuo. The crude product was purified by chromatography on silica gel to yield the title compound (12 g, 72%). $^1$H NMR (CDCl$_3$) δ 8.73 (br s, 1H), 6.82 (s, 2H), 6.76 (s, 1H), 5.95 (br s, 1H), 5.16–5.23 (m, 2H), 3.7–4.15 (m, 3H), 1.45–2.0 (m, 8H). IR (NaCl) 3177, 2956, 1590, 1433, 1373, 1289, 935 cm$^{-1}$.

5. [5-Chloro-3-(1,2-oxazaperhydroin-5-ylmethoxy)phenyl]-N-cyclopentyl-N-prop-2-enylcarboxamide To a solution of the product (203 mg, 0.726 mmol), as prepared in the preceding step, and tert-butyl 5-(hydroxymethyl)-1,2-oxazaperhydroine-2-carboxylate (166 mg, 0.765 mmol), the product of step 8 of Example 1, in tetrahydrofuran (10 mL) were added triphenylphosphine (247 mg, 0.943 mmol) and diethyl azodicarboxylate (165 mg, 0.948 mmol) at room temperature. After stirring overnight, the reaction solution was concentrated and flash chromatographed (SiO$_2$) to give a clear oil. The oil (320 mg, 0.669 mmol) in dichloromethane (5 mL) was treated with trifluoroacetic acid (2 mL) for 1 h at room temperature. The solution was concentrated, and the residue was partitioned between dichloromethane and saturated sodium bicarbonate. The organic layer was dried, concentrated, and flash chromatographed to give the title compound as a clear oil (232 mg, 84.4%). $^1$H NMR (CDCl$_3$) δ 6.94 (m, 1H), 6.90 (m, 1H), 6.78–6.77 (m, 1H), 5.18 (dd, 2H, J=1.2, 10.3 Hz), 4.18–4.17 (m, 2H), 3.97 (m, 2H), 3.91–3.83 (m, 3H), 3.71 (dd, 1H, J=9.1, 11.6 Hz), 3.22–3.19 (m, 2H), 2.29 (m, 1H), 1.95–1.91 (m, 1H), 1.69–1.62 (m, 6H), 1.49 (m, 2H), 1.28 (t, 2H, J=7.1 Hz).

6. tert-Butyl-2-aza-3-[(tert-butoxy)carbonylamino]-3-(5-{[5-chloro-3-(N-cyclopentyl-N-prop-2-enylcarbamoyl)phenoxy]methyl}(1,2-oxazaperhydroin-2-yl))prop-2-enoate To a solution of the product (68 mg, 0.18 mmol) of the preceding step in N,N-dimethylformamide (3 mL) was added N,N'-bis(tert-butoxycarbonyl)-1H-pyrazole-1-carboxamidine (62 mg, 0.20 mmol). After stirring at 42° C. overnight, the solvent was evaporated and the residue was flash chromatographed to yield the title compound as a clear oil (28 mg, 25%). $^1$H NMR (CDCl$_3$) δ 9.06 (s(br), 1H), 6.95 (s, 1H), 6.90 (s, 1H), 6.77 (m, 1H), 5.94 (s(br), 1H), 5.18 (dd, 1H, J=1.1, 10.3 Hz), 4.27–4.19 (m, 2H), 3.97–3.83 (m, 7H), 3.48–3.41 (m, 1H), 2.40–2.38 (m 1H), 1.95–1.91 (m, 1H), 1.75–1.66 (m, 9H), 1.50 (s, 18H).

7. 5-{[5-Chloro-3-(N-cyclopentyl-N-prop-2-enylcarbamoyl)phenoxy]methyl}-1,2-oxazaperhydroine-2-carboxamidine trifluoroacetate The product (32 mg, 0.052 mmol) of the preceding step in dichloromethane (1 mL) was treated with trifluoroacetic acid (1 mL) for 0.5 h. The solution was concentrated and the residue was purified on Waters' sep-pak (SiO$_2$, 5 g) to obtain the title compound as white foam (27 mg, 100%). $^1$H NMR (CDCl$_3$/MeOH-d$_4$) δ 6.95 (s, 2H), 6.78 (s, 1H), 5.95–5.77 (m, 1H), 5.20 (d, 2H, J=10.3 Hz), 4.34 (dd, 1H, J=3.8, 11.4 Hz), 4.07–3.91 (m, 6H), 3.61–3.54 (m, 1H), 2.48 (m, 1H), 2.05–2.01 (m 1H), 1.83–1.69 (m, 7H), 1.49 (m, 1H). Mass spectrum (LCMS, ESI) calcd. for C$_{21}$H$_{29}$ClN$_4$O$_3$: 421.5 (M+H). Found: 421.5.

EXAMPLE 4

In vitro Inhibition of Purified Enzymes

Reagents: All buffer salts were obtained from Sigma Chemical Company (St. Louis, Mo.), and were of the highest purity available. The enzyme substrates, N—N-benzoyl-Phe-Val-Arg-p-nitroanilide (Sigma B7632), N-benzoyl-Ile-Glu-Gly-Arg-p-nitroanilide hydrochloride (Sigma B2291), N-p-Tosyl-Gly-Pro-Lys-p-nitroanilide (Sigma T6140), N-succinyl-Ala-Ala-Pro-Phe-p-nitroanilide (Sigma S7388) and N-CBZ-Val-Gly-Arg-p-nitroanilide (Sigma C7271) were obtained from Sigma. N-succinyl-Ala-Ala-Pro-Arg-p-nitroanilide (BACHEM L-1720) and N-succinyl-Ala-Ala-Pro-Val-p-nitroanilide (BACHEM L-1770) were obtained from BACHEM (King of Prussia, Pa.).

Human α-thrombin, human factor Xa and human plasmin were obtained from Enzyme Research Laboratories (South Bend, Ind.). Bovine α-chymotrypsin (Sigma C4129), bovine trypsin (Sigma T8642) and human kidney cell urokinase (Sigma U5004) were obtained from Sigma. Human leukocyte elastase was obtained from Elastin Products (Pacific, Mo.).

$K_i$ Determinations: All assays are based on the ability of the test compound to inhibit the enzyme catalyzed hydrolysis of a peptide p-nitroanilide substrate. In a typical $K_i$ determination, substrate is prepared in DMSO, and diluted into an assay buffer consisting of 50 mM HEPES, 200 mM NaCl, pH 7.5. The final concentrations for each of the substrates is listed below. In general, substrate concentrations are lower than the experimentally determined value for $K_m$. Test compounds are prepared as a 1.0 mg/ml solution in DMSO. Dilutions are prepared in DMSO yielding 8 final concentrations encompassing a 200 fold concentration range. Enzyme solutions are prepared at the concentrations listed below in assay buffer.

In a typical $K_i$ determination, into each well of a 96 well plate is pipetted 280 μL of substrate solution, 10 μL of test compound solution, and the plate allowed to thermally equilibrate at 37° C. in a Molecular Devices plate reader for >15 minutes. Reactions were initiated by the addition of a 10 μL aliquot of enzyme and the absorbance increase at 405 nm is recorded for 15 minutes. Data corresponding to less than 10% of the total substrate hydrolysis were used in the calculations. The ratio of the velocity (rate of change in absorbance as a function of time) for a sample containing no test compound is divided by the velocity of a sample containing test compound, and is plotted as a function of test compound concentration. The data are fit to a linear regression, and the value of the slope of the line calculated. The inverse of the slope is the experimentally determined $K_i$ value.

Thrombin: Thrombin activity was assessed as the ability to hydrolyze the substrate N-succinyl-Ala-Ala-Pro-Arg-p-nitroanilide. Substrate solutions were prepared at a concentration of 32 μM (32 μM<<$K_m$=180 μM) in assay buffer. Final DMSO concentration was 4.3%. Purified human α-thrombin was diluted into assay buffer to a concentration of 15 nM. Final reagent concentrations were: [thrombin]= 0.5 nM, [substrate N-succinyl-Ala-Ala-Pro-Arg-p-nitroanilide]=32 μM.

Factor X [FXa]: FXa activity was assessed as the ability to hydrolyze the substrate N-benzoyl-Ile-Glu-Gly-Arg-p-nitroanilide hydrochloride. Substrate solutions were prepared at a concentration of 51 μM (51<<$K_m$=1.3 mM) in assay buffer. Final DMSO concentration was 4.3%. Purified activated human Factor X was diluted into assay buffer to a concentration of 300 nM. Final reagent concentrations were: [FXa]=10 nM, [N-benzoyl-Ile-Glu-Gly-Arg-p-nitroanilide hydrochloride]=51 μM.

Plasmin: Plasmin activity was assessed as the ability to hydrolyze the N-p-Tosyl-Gly-Pro-Lys-p-nitroanilide. Substrate solutions were prepared at a concentration of 37 μM (37 μM<<$K_m$=243 μM) in assay buffer. Final DMSO concentration was 4.3%. Purified human plasmin was diluted into assay buffer to a concentration of 240 nM. Final reagent concentrations were: [Plasmin]=8 nM, [N-p-Tosyl-Gly-Pro-Lys-p-nitroanilide]=37 μM.

Chymotrypsin: Chymotrypsin activity was assessed as the ability to hydrolyze N-succinyl-Ala-Ala-Pro-Phe-p-nitroanilide. Substrate solutions were prepared at a concentration of 14 μM (14 μM<<$K_m$=62 μM) in assay buffer. Final DMSO concentration was 4.3%. Purified bovine chymotrypsin was diluted into assay buffer to a concentration of 81 nM. Final reagent concentrations were: [Chymotrypsin]=2.7 nM, [N-succinyl-Ala-Ala-Pro-Phe-p-nitroanilide]=14 μM.

Trypsin: Trypsin activity was assessed as the ability to hydrolyze N-benzoyl-Phe-Val-Arg-p-nitroanilide. Substrate solutions were prepared at a concentration of 13 μM (13 μM<<$K_m$=291 μM) in assay buffer. Final DMSO concentration was 4.3%. Purified bovine trypsin was diluted into assay buffer to a concentration of 120 nM. Final reagent concentrations were: [Trypsin]=4 nM, [N-benzoyl-Phe-Val-Arg-p-nitroanilide]=13 μM.

Elastase: Elastase activity was assessed as the ability to hydrolyze N-succinyl-Ala-Ala-Pro-Val-p-nitroanilide. Substrate solutions were prepared at a concentration of 19 μM (19 μM<<$K_m$=89 μM) in assay buffer. Final DMSO concentration was 4.3%. Purified human leukocyte elastase was diluted into assay buffer to a concentration of 750 nM. Final reagent concentrations were: [Elastase]=25 nM, [N-succinyl-Ala-Ala-Pro-Val-p-nitroanilide]=19 μM.

Urokinase: Urokinase activity was assessed as the ability to hydrolyze N-CBZ-Val-Gly-Arg-p-nitroanilide. Substrate solutions were prepared at a concentration of 100 μM (100 μM<$K_m$=1.2 mM) in assay buffer. Final DMSO concentration was 4.3%. Purified human kidney urokinase was diluted into assay buffer to a concentration of 1.2 μM. Final reagent concentrations were: [Urokinase]=40 nM, and N-CBZ-Val-Gly-Arg-p-nitroanilide]=100 mM.

The results of screening the compounds of Examples 1–3 demonstrate that compounds of the invention are potent inhibitors of thrombin. A $K_i$ value of 7 nM was measured for the compound of Example 1 using the thrombin assay, while $K_i$ values of 13 nM and 8 nM were measured for the compounds of Examples 2 and 3, respectively.

Having now fully described this invention, it will be understood to those of ordinary skill in the art that the same can be performed within a wide and equivalent range of conditions, formulations, and other parameters without affecting the scope of the invention or any embodiment thereof. All patents and publications cited herein are fully incorporated by reference herein in their entirety.

What is claimed is:

1. A compound of Formula I:

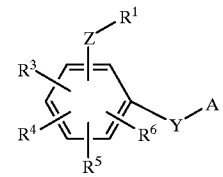

or a solvate, hydrate or pharmaceutically acceptable salt thereof, wherein:

$R^1$ is one of alkyl, cycloalkyl, alkenyl, alkynyl, aryl, aralkyl or heteroaryl, any of which is optionally substituted;

Z is one of —$OSO_2$—, —$SO_2O$—, —$OC(R^yR^z)$—, or —$C(R^yR^z)O$—;

$R^y$ and $R^z$ are each independently one of hydrogen, alkyl, cycloalkyl, aryl, aralkyl, hydroxyalkyl, carboxyalkyl, aminoalkyl, monoalkylaminoalkyl, dialkylaminoalkyl or carboxy;

$R^3$, $R^4$, $R^5$ and $R^6$ are each independently one of hydrogen, alkyl, cycloalkyl, alkenyl, alkynyl, optionally substituted aryl, optionally substituted aralkyl, optionally substituted heteroaryl, trifluoromethyl, halogen, hydroxyalkyl, cyano, nitro, carboxamido, —$CO_2R^x$, —$CH_2OR^x$ or —$OR^x$, or when present on adjacent carbon atoms, $R^4$ and $R^3$ may also be taken together to form one of —CH=CH—CH=CH— or —$(CH_2)_q$—, where q is from 2 to 6, and $R^5$ and $R^6$ are defined as above;

$R^x$, in each instance, is independently one of hydrogen, alkyl or cycloalkyl wherein said alkyl or cycloalkyl groups may optionally have one or more unsaturations;

Y is one of —O—, —$NR^{10}$—, —S—, —$CHR^{10}$— or a covalent bond; and $R^{10}$, in each instance, is independently one of hydrogen, alkyl, aralkyl, aryl, hydroxy($C_{2-10}$)alkyl, amino($C_{2-10}$)alkyl, monoalkylamino($C_{2-10}$)alkyl, dialkylamino($C_{2-10}$)alkyl or carboxyalkyl;

A is one of

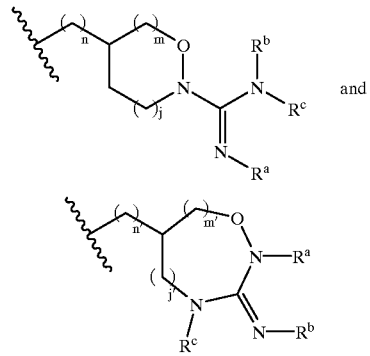

and wherein:

$R^a$, $R^b$ and $R^c$ are independently hydrogen, alkyl, hydroxy, alkoxy, aryloxy, aralkoxy, alkoxycarbonyloxy, cyano or —$CO_2R^w$, where $R^w$ is alkyl, cycloalkyl, phenyl, benzyl,

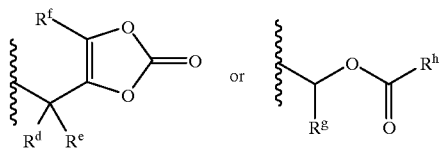

where $R^d$ and $R^e$ are independently hydrogen, $C_{1-6}$ alkyl, $C_{2-6}$ alkenyl or phenyl, $R^f$ is hydrogen, $C_{1-6}$ alkyl, $C_{2-6}$ alkenyl or phenyl, $R^g$ is hydrogen, $C_{1-6}$ alkyl, $C_{2-6}$ alkenyl or phenyl, and $R^h$ is aralkyl or alkyl;

n and n' are each from zero to 4;

m is from zero to 2;

m' is zero or 1; and j and j' are each from zero to 2;

provided that n, n', m, m', j and j' are not all zero.

2. A compound of claim 1 having the Formula Ia:

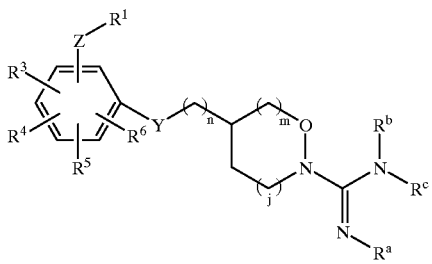

or a solvate, hydrate or pharmaceutically acceptable salt thereof, wherein $R^1$, Z, $R^3$, $R^4$, $R^5$, $R^6$, Y, $R^a$, $R^b$, $R^c$, n, m and j are as defined in claim 1.

3. A compound of claim 1 having the Formula Ib:

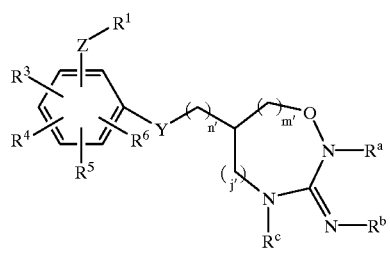

or a solvate, hydrate or pharmaceutically acceptable salt thereof, wherein $R^1$, Z, $R^3$, $R^4$, $R^5$, $R^6$, Y, $R^a$, $R^b$, $R^c$, n', m' and j' are as defined in claim 1.

4. A compound of claim 1, wherein:

$R^1$ is one of $C_{6-10}$ aryl, pyridinyl, thiophenyl, quinazolinyl, quinolinyl or tetrahydroquinolinyl, any of which is optionally substituted by one or two of hydroxy, nitro, trifluoromethyl, halogen, $C_{1-6}$ alkyl, $C_{6-10}$ aryl, $C_{1-6}$ alkoxy, $C_{6-10}$ ar($C_{1-6}$)alkoxy, $C_{1-6}$ aminoalkyl, $C_{1-6}$ aminoalkoxy, amino, mono($C_{1-4}$) alkylamino, di($C_{1-4}$)alkylamino, $C_{2-6}$ alkoxycarbonylamino, $C_{2-6}$ alkoxycarbonyl, carboxy, $C_{1-6}$ hydroxyalkyl, $C_{2-6}$ hydroxyalkoxy, ($C_{1-6}$)alkoxy($C_{2-6}$)alkoxy, mono- and di-$C_{1-4}$ alkylamino($C_{2-6}$) alkoxy, $C_{2-10}$ mono(carboxyalkyl)amino, di($C_{2-10}$ carboxyalkyl)amino, $C_{1-4}$ ar($C_{1-6}$) alkoxycarbonyl, $C_{2-6}$ alkynylcarbonyl, $C_{1-6}$ alkylsulfonyl, $C_{2-6}$ alkenylsulfonyl, $C_{2-6}$ alkynylsulfonyl, $C_{6-10}$ arylsulfonyl, $C_{6-10}$ ar($C_{1-6}$) alkylsulfonyl, $C_{1-6}$ alkylsulfinyl, $C_{1-6}$ alkylsulfonamido, $C_{6-10}$ arylsulfonamido, $C_{6-10}$ ar($C_{1-6}$)alkylsulfonamido, amidino, guanidino, $C_{1-6}$ alkyliminoamino, formyliminoamino, $C_{2-6}$ carboxyalkoxy, $C_{2-6}$ carboxyalkyl, carboxyalkylamino, cyano, trifluoromethoxy, perfluoroethoxy and $R^{13}R^{14}NSO_2$—;

$R^{13}$ and $R^{14}$ are independently selected from the group consisting of hydrogen, alkyl, cycloalkyl, alkenyl, alkynyl, aryl, aralkyl, heterocycle, heterocycloalkyl, carboxyalkyl, alkoxycarbonylalkyl, cyano($C_{2-10}$) alkyl, hydroxy($C_{2-10}$)alkyl, alkoxy($C_{2-10}$)alkyl, mono- and di-alkylamino($C_{2-10}$)alkyl, or $R^{13}$ and $R^{14}$ can be taken together with the nitrogen atom to which they are attached to form a three to seven membered ring, optionally containing one or more heteroatoms in addition to said nitrogen, such as oxygen, sulfur, or nitrogen ($NR^{15}$), and said ring having one or two optional substituents selected from the group consisting of hydroxy, acyloxy, alkoxy, aryloxy, amino, mono- and di-alkylamino, acylamino, alkyl, cycloalkyl, alkenyl, alkynyl, aryl, aralkyl, heterocycle, heterocycloalkyl, carboxyalkyl, alkoxycarbonylalkyl, cyano($C_{2-10}$)alkyl, hydroxy($C_{2-10}$)alkyl, alkoxy($C_{2-10}$)alkyl, mono- and di-alkylamino($C_{2-10}$)alkyl, carboxy, alkoxycarbonyl, carboxamido, formyl, alkanoyl, aroyl, aralkanoyl, sulfonyl, alkylsulfonyl, alkoxysulfonyl, sulfonamido, phosphonyl, phosphoramido, and phosphinyl, and wherein $R^{15}$ is selected from the group consisting of hydrogen, alkyl, cycloalkyl, alkenyl, alkynyl, aryl, aralkyl, heterocycle, heterocycloalkyl, carboxyalkyl, alkoxycarbonylalkyl, cyano($C_{2-10}$)alkyl, hydroxy($C_{2-10}$)alkyl, alkoxy($C_{2-10}$)alkyl, mono- and di-alkylamino($C_{2-10}$)alkyl, carboxy, alkoxycarbonyl, carboxamido, formyl, alkanoyl, aroyl, aralkanoyl, sulfonyl, alkylsulfonyl, alkoxysulfonyl, sulfonamido, phosphonyl, phosphoramido, and phosphinyl; and Z is one of —$SO_2O$—, —$OSO_2$—, —$C(R^yR^z)O$— or —$OC(R^yR^z)$—, where $R^y$ and $R^z$ are each hydrogen.

5. A compound of claim 4, wherein Z is —$SO_2O$—.

6. A compound of claim 1, wherein:

$R^1$ is one of phenyl, naphthyl, pyridyl, thiophenyl, quinolinyl or isoquinolinyl, optionally substituted by one or two of chloro, methoxy, methyl, trifluoromethyl, methylsulfonyl, cyano, nitro, amino or dimethylamino;

Z is —$SO_2O$—;

$R^3$ and $R^4$ are hydrogen or $C_{1-4}$ alkyl, or $R^3$ and $R^4$ may also be taken together to form —CH=CH—CH=CH—;

$R^5$ is one of hydrogen, methyl, methoxy or trifluoromethyl;

$R^6$ is hydrogen;

Y is one of O, $NR^{10}$ or a covalent bond; and $R^{10}$, in each instance, is independently hydrogen, $C_{1-4}$ alkyl, $C_{2-4}$ hydroxyalkyl, $C_{2-4}$ carboxyalkyl, $C_{2-4}$ aminoalkyl, dimethylamino($C_{2-8}$)alkyl, or methylamino($C_{2-8}$)alkyl.

7. A compound of claim 1, wherein:

$R^1$ is phenyl, substituted by one of alkylsulfonyl, arylsulfonyl and $R^{13}R^{14}NSO_2$—, where $R^{13}$ and $R^{14}$ are independently selected from the group consisting of hydrogen, $C_{1-6}$ alkyl, $C_{3-7}$ cycloalkyl, $C_{2-6}$ alkenyl, $C_{2-6}$ alkynyl, $C_{6-10}$ aryl, $C_{6-10}$ ar($C_{1-4}$)alkyl, pyridyl, pyridyl($C_{1-4}$)alkyl, carboxy($C_{1-6}$)alkyl, $C_{1-4}$ alkoxycarbonyl($C_{1-4}$)alkyl, cyano($C_{2-6}$)alkyl, hydroxy($C_{2-6}$)alkyl, $C_{1-4}$ alkoxy($C_{2-6}$)alkyl, mono- and di-($C_{1-4}$)alkylamino($C_{2-6}$)alkyl, or $R^{13}$ and $R^{14}$ can be taken together with the nitrogen atom to which they are attached to form a heterocyclic ring selected from the group consisting of N-morpholinosulfonyl, N-piperazinylsulfonyl (optionally N' substituted with $C_{1-6}$ alkyl, $C_{1-6}$ hydroxyalkyl, $C_{6-10}$ aryl, $C_{6-10}$ aryl($C_{1-6}$)alkyl, $C_{1-6}$ alkylsulfonyl, $C_{6-10}$ arylsulfonyl, $C_{1-6}$ alkylcarbonyl, morpholino or arylcarbonyl), N-pyrrolylsulfonyl, N-piperidinylsulfonyl, N-pyrrolidinylsulfonyl, N-dihydropyridylsulfonyl, N-indolylsulfonyl, wherein said heterocyclic ring can be optionally substituted with one or two of hydroxy, $C_{1-8}$ alkanoyloxy, $C_{1-6}$ alkoxy, $C_{6-10}$ aryloxy, amino, mono- and di-$C_{1-6}$ alkylamino, $C_{1-8}$ alkanoylamino, $C_{1-4}$ alkyl, $C_{3-7}$ cycloalkyl, $C_{6-10}$ aryl, $C_{6-10}$ ar($C_{1-4}$)alkyl, heterocycle, heterocycloalkyl, carboxy($C_{1-6}$)alkyl, $C_{1-4}$ alkoxycarbonyl($C_{1-4}$)alkyl, cyano($C_{2-6}$)alkyl, hydroxy($C_{2-6}$)alkyl, $C_{1-4}$ alkoxy($C_{2-6}$)alkyl, mono- and di-($C_{1-4}$)alkylamino($C_{2-6}$)alkyl, carboxy, $C_{1-6}$ alkoxycarbonyl, carboxamido, formyl, $C_{1-6}$ alkanoyl, $C_{6-10}$ aroyl, $C_{6-10}$ ar($C_{1-4}$)alkanoyl, sulfonyl, $C_{1-6}$ alkylsulfonyl, $C_{1-6}$ alkoxysulfonyl, sulfonamido, phosphonyl, phosphoramido, or phosphinyl;

Z is one of —SO$_2$O—, —CH$_2$O— or —OCH$_2$—;

$R^3$ and $R^4$ are hydrogen or $C_{1-4}$ alkyl, or $R^3$ and $R^4$ may also be taken together to form —CH=CH—CH=CH—;

$R^5$ is one of hydrogen, methyl, methoxy or trifluoromethyl;

$R^6$ is hydrogen;

Y is one of O, NR$^{10}$ or a covalent bond; and $R^{10}$, in each instance, is independently hydrogen, $C_{1-4}$ alkyl, $C_{2-4}$ hydroxyalkyl, $C_{2-4}$ carboxyalkyl, $C_{2-4}$ aminoalkyl, dimethylamino($C_{2-8}$)alkyl, or methylamino($C_{2-8}$)alkyl.

8. A compound of claim 1, wherein the moiety —Z—R$^1$ of Formula I is attached to the benzene ring in a meta-position to the Y substituent.

9. A compound of claim 1, wherein Y is one of —O—, —NR$^{10}$— or a covalent bond, and Z is one of —SO$_2$O— or —CH$_2$O—.

10. A compound of claim 1, wherein Y is —O— and Z is —SO$_2$O—.

11. A compound of claim 1, wherein the optional substituent on R$^1$ is selected from the group consisting of hydroxy, nitro, trifluoromethyl, halogen, $C_{1-6}$ alkyl, $C_{1-6}$ alkoxy, $C_{1-6}$ aminoalkyl, $C_{6-10}$ aryl, $C_{6-10}$ ar($C_{1-6}$)alkoxy, biphenyl($C_{1-6}$)alkoxy $C_{1-6}$ aminoalkoxy, amino, mono($C_{1-4}$)alkylamino, di($C_{1-4}$)alkylamino, $C_{2-6}$ alkoxycarbonylamino, $C_{2-6}$ alkoxycarbonyl, carboxy, $C_{1-6}$ hydroxyalkyl, $C_{2-10}$ mono(carboxyalkyl)amino, bis($C_{2-10}$ carboxyalkyl)amino, $C_{6-14}$ ar($C_{1-6}$)alkoxycarbonyl, $C_{2-6}$ alkynylcarbonyl, $C_{1-6}$ alkylsulfonyl, $C_{6-10}$ arylsulfonyl, $C_{2-6}$ alkenylsulfonyl, $C_{2-6}$ alkynylsulfonyl, $C_{1-6}$ alkylsulfinyl, $C_{1-6}$ alkylsulfonamido, amidino, guanidino, $C_{1-6}$ alkyliminoamino, formyliminoamino, $C_{2-6}$ carboxyalkoxy, carboxyalkylamino, cyano, trifluoromethoxy, and perfluoroethoxy.

12. A compound of claim 1, wherein the optional stubstituent on R$^1$ is selected from the group consisting of $C_{1-6}$ alkylsulfonyl, $C_{6-10}$ arylsulfonyl, $C_{6-10}$ ar($C_{1-6}$) alkylsulfonyl, $C_{6-10}$ arylsulfonamido, $C_{6-10}$ ar($C_{1-6}$) alkylsulfonamido, N-morpholinosulfonyl, and $R^{13}R^{14}NSO_2$—, wherein $R^{13}$ and $R^{14}$ are independently selected from the group consisting of hydrogen, $C_{1-6}$ alkyl, $C_{3-7}$ cycloalkyl, $C_{2-6}$ alkenyl, $C_{2-6}$ alkynyl, $C_{6-10}$ aryl, $C_{6-10}$ ar($C_{1-4}$) alkyl, pyridyl, pyridyl($C_{1-4}$)alkyl, carboxy($C_{1-6}$)alkyl, $C_{1-4}$ alkoxycarbonyl($C_{1-4}$)alkyl, cyano($C_{2-6}$)alkyl, hydroxy($C_{2-6}$)alkyl, $C_{1-4}$ alkoxy($C_{2-6}$)alkyl, mono- and di-($C_{1-4}$)alkylamino($C_{2-6}$)alkyl, or $R^{13}$ and $R^{14}$ can be taken together with the nitrogen atom to which they are attached to form a heterocyclic ring selected from the group consisting of N-morpholino, N-piperazinyl (optionally N' substituted with $C_{1-6}$ alkyl, $C_{1-6}$ hydroxyalkyl, $C_{6-10}$ aryl, $C_{6-10}$ aryl($C_{1-6}$) alkyl, $C_{1-6}$ alkylsulfonyl, $C_{6-10}$ arylsulfonyl, $C_{1-6}$ alkylcarbonyl, morpholino or $C_{6-10}$ arylcarbonyl, N-pyrrolyl, N-piperidinyl, N-pyrrolidinyl, N-dihydropyridyl, and N-indolyl, wherein:

said heterocyclic ring can be optionally substituted with one or two of hydroxy, $C_{1-8}$ alkanoyloxy, $C_{1-6}$ alkoxy, $C_{6-10}$ aryloxy, amino, mono- and di-$C_{1-6}$ alkylamino, $C_{1-8}$ alkanoylamino, $C_{1-4}$ alkyl, $C_{3-7}$ cycloalkyl, $C_{6-10}$ aryl, $C_{6-10}$ ar($C_{1-4}$)alkyl, heterocycle, heterocycloalkyl, carboxy($C_{1-6}$)alkyl, $C_{1-4}$ alkoxycarbonyl($C_{1-4}$)alkyl, cyano($C_{2-6}$)alkyl, hydroxy($C_{2-6}$)alkyl, $C_{1-4}$ alkoxy($C_{2-6}$)alkyl, mono- and di-($C_{1-4}$)alkylamino($C_{2-6}$)alkyl, carboxy, $C_{1-6}$ alkoxycarbonyl, carboxamido, formyl, $C_{1-6}$ alkanoyl, $C_{6-10}$ aroyl, $C_{6-10}$ ar($C_{1-4}$)alkanoyl, sulfonyl, $C_{1-6}$ alkylsulfonyl, $C_{1-6}$ alkoxysulfonyl, sulfonamido, phosphonyl, phosphoramido, or phosphinyl.

13. A compound of claim 1, wherein R$^1$ is heteroaryl or substituted heteroaryl.

14. A compound of claim 13, wherein R$^1$ is selected from the group consisting of pyridyl, pyrazolyl, thiophenyl, chromenyl, benzoxazolyl, benzthiadiazolyl, quinazolinyl, quinolinyl, isoquinolinyl and tetrahydroquinolinyl, any of which is optionally substituted.

15. A compound of claim 14, wherein R$^1$ is selected from the group consisting of thiophenyl, isoquinolinyl and quinolinyl.

16. A compound of claim 14, wherein R$^1$ is substituted with 1 to 3 substituents independently selected from the group consiting of halogen, $C_{1-6}$ alkyl, $C_{1-6}$ alkoxy, amidino, guanidino, carboxyalkoxy, carboxyalkylamino, amino, mono($C_{1-6}$)alkylamino and di($C_{1-6}$)alkylamino.

17. A compound of claim 1, wherein R$^3$, R$^4$, R$^5$ and R$^6$ are independently hydrogen, $C_{1-4}$ alkyl, $C_{4-7}$ cycloalkyl, $C_{6-14}$ aryl, $C_{6-10}$ ar($C_{1-4}$)alkyl, trifluoromethyl, halogen, hydroxyalkyl, cyano, nitro, carboxamide, carboxy, alkoxycarbonyl, carboxymethyl, alkoxycarbonylmethyl, or cycloalkyloxycarbonyl.

18. A compound of claim 1, wherein:

R$^1$ is one of $C_{6-10}$ aryl, pyridinyl, thiophenyl, quinazolinyl, quinolinyl or tetrahydroquinolinyl, any of which is optionally substituted by one or two of hydroxy, nitro, trifluoromethyl, halogen, $C_{1-6}$ alkyl, $C_{1-6}$ alkoxy, $C_{1-6}$ aminoalkyl, $C_{1-6}$ aminoalkoxy, amino, mono($C_{1-4}$)alkylamino, di($C_{1-4}$)alkylamino, $C_{2-6}$ alkoxycarbonylamino, $C_{2-6}$ alkoxycarbonyl, carboxy, $C_{1-6}$ hydroxyalkyl, $C_{2-6}$ hydroxyalkoxy, $C_{2-10}$ mono(carboxyalkyl)amino, bis($C_{2-10}$ carboxyalkyl) amino, $C_{6-14}$ ar($C_{1-6}$)alkoxycarbonyl, $C_{2-6}$ alkynylcarbonyl, $C_{1-6}$ alkylsulfonyl, $C_{2-6}$ alkenylsulfonyl, $C_{2-6}$ alkynylsulfonyl, $C_{1-6}$ alkylsulfinyl, $C_{1-6}$ alkylsulfonamido, amidino, guanidino, $C_{1-6}$ alkyliminoamino, formyliminoamino, $C_{2-6}$ carboxyalkoxy, $C_{2-6}$ carboxyalkyl, carboxyalkylamino, cyano, trifluoromethoxy, and perfluoroethoxy;

$R^3$, $R^4$, $R^5$ and $R^6$ are independently one of hydrogen, $C_{1-4}$ alkyl, $C_{3-8}$ cycloalkyl, phenyl, benzyl, trifluoromethyl, halogen, hydroxy($C_{1-4}$)alkyl, cyano, nitro, carboxamido, carboxy, $C_{1-4}$ alkoxycarbonyl, $C_{1-4}$ alkoxymethyl or $C_{1-4}$ alkoxy; or alternatively, $R^4$ and $R^3$, when present on adjacent carbon atoms, may also be taken together to form one of —CH=CH—CH=CH— or —(CH$_2$)$_q$—, where q is from 2 to 6, and $R^5$ and $R^6$ are as defined in claim 1;

Y is one of —O—, —S—, —NR$^{10}$—, or a covalent bond; and $R^{10}$, in each instance, is independently hydrogen, $C_{1-6}$ alkyl, benzyl, phenyl, $C_{2-10}$ hydroxyalkyl, $C_{2-10}$ aminoalkyl, $C_{1-4}$ monoalkylamino($C_{2-8}$)alkyl, $C_{1-4}$ dialkylamino($C_{2-8}$)alkyl or $C_{2-10}$ carboxyalkyl.

19. A compound of claim 1, wherein $R^{10}$ is selected from the group consisting of hydrogen, $C_{1-6}$ alkyl, $C_{6-10}$ ar($C_{1-6}$)alkyl, $C_{6-10}$ aryl, $C_{2-10}$ hydroxyalkyl $C_{2-10}$ aminoalkyl, $C_{2-7}$ carboxyalkyl, mono($C_{1-4}$ alkyl)amino($C_{1-8}$)alkyl, and di($C_{1-4}$ alkyl)amino ($C_{1-8}$)alkyl.

20. A compound of claim 1, wherein $R^a$, $R^b$ and $R^c$ are independently one of hydrogen, hydroxy, $C_{1-6}$ alkyl, $C_{1-6}$ alkoxy, cyano or —CO$_2$R$^w$, where $R^w$, in each instance, is one of $C_{1-4}$alkyl, $C_{4-7}$cycloalkyl or benzyloxycarbonyl.

21. A compound of claim 20, wherein $R^a$, $R^b$ and $R^c$ are each hydrogen.

22. A compound of claim 1, wherein $R^a$, $R^b$ or $R^c$ is the group —CO$_2$R$^w$, where $R^w$ is one of

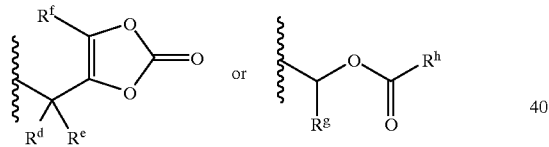

where $R^d$–$R^h$ are defined as in claim 1.

23. A compound of claim 22, wherein each of $R^d$, $R^e$ and $R^g$ is hydrogen, $R^f$ is methyl, and $R^h$ is benzyl or tert-butyl.

24. A compound of claim 1, wherein m, m', n, n', j, and j' are independently 0 or 1, provided that m, m', n, n', j, and j' are not all zero.

25. A compound having the formula II:

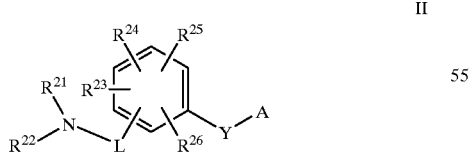

II or a solvate, hydrate or pharmaceutically acceptable salt thereof; wherein:

L represents —C(O)—, C(R$^{2Y}$R$^{2Z}$), or —SO$_2$—;

$R^{2Y}$ and $R^{2Z}$ are each independently one of hydrogen, alkyl, cycloalkyl, aryl, aralkyl, hydroxyalkyl, carboxyalkyl, aminoalkyl, mono alkylaminoalkyl, dialkylaminoalkyl or carboxy;

$R^{21}$ represents a group:

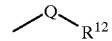

$R^{22}$ represents a group:

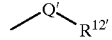

or $R^{21}$ and $R^{22}$ can be taken together with the nitrogen atom to which they are attached to form a three to seven membered ring, either of which contains an additional nitrogen or oxygen atom, and which is optionally benzo- or pyrido-fused, and said ring having one or two optional substituents on either a ring carbon or nitrogen selected from the group consisting of halogen, hydroxy, acyloxy, alkoxy, aryloxy, alkyl, cycloalkyl, alkenyl, alkynyl, aryl, aralkyl, heteroaryl, heteroar($C_{1-4}$)alkyl, carboxyalkyl, alkoxycarbonylalkyl, hydroxyalkoxyalkyl, cyano($C_{2-10}$)alkyl, hydroxy($C_{2-10}$)alkyl, alkoxy($C_{2-10}$)alkyl, alkoxyalkyl, mono- and di-alkylamino($C_{2-10}$)alkyl, carboxy, alkoxycarbonyl, carboxamido, formyl, alkanoyl, aroyl, aralkanoyl, sulfonyl, alkylsulfonyl, alkoxysulfonyl, and NR$^{13}$R$^{14}$ (when C-substituted);

$R^{12}$ and $R^{12'}$ independently represent hydrogen, $C_{3-7}$ cycloalkyl, $C_{3-7}$ cycloalkenyl, $C_{3-7}$ heterocycloalkyl, $C_{3-7}$ heterocycloalkenyl, aryl, or heteroaryl, which groups are optionally substituted with $C_{1-6}$ alkyl or hydroxy, or $R^{12}$ and $R^{12'}$ independently represent diarylmethyl, diheteroarylmethyl, dicycloalkylmethyl or (aryl)(heteroaryl)CH—;

Q and Q' independently represent a bond, a $C_{1-6}$ alkyl chain, a $C_{3-6}$ alkenyl chain, or a $C_{3-6}$ alkynyl chain, where one or two nitrogen, oxygen, or sulfur atoms may be optionally contained within each chain, and the chains are optionally substituted by one or more groups selected from halogen, hydroxy, CN, $C_{1-6}$ alkyl, $C_{1-6}$ alkoxy, $C_{1-6}$ alkoxy($C_{1-6}$)alkyl, $C_{1-6}$ acyloxy, NR$^{13}$R$^{14}$, NHCOR$^{15}$, NHSO$_2$R$^{16}$, COR$^{15}$, CO$_2$R$^{15}$, CONR$^{13}$R$^{14}$, and SO$_2$NR$^{17}$R$^{18}$;

$R^{13}$–$R^{16}$ represent hydrogen, $C_{1-6}$ alkyl, $C_{3-7}$ cycloalkyl, $C_{2-6}$ alkenyl, $C_{2-6}$ alkynyl, $C_{6-10}$ aryl, mono- or di-hydroxy($C_{6-10}$)aryl, $C_{6-10}$ ar($C_{1-4}$)alkyl, pyridyl, pyridyl($C_{1-4}$)alkyl, carboxy($C_{1-6}$)-alkyl, $C_{1-4}$ alkoxycarbonyl($C_{1-4}$)alkyl, cyano($C_{2-6}$)alkyl, hydroxy ($C_{2-6}$)alkyl, $C_{1-4}$ alkoxy($C_{2-6}$)alkyl, mono- and di-($C_{1-4}$)alkylamino($C_{2-6}$)alkyl;

or $R^{13}$ and $R^{14}$ form a $C_{3-7}$ heterocycloalkyl ring, or $R^{16}$ additionally may represent trifluoromethyl;

$R^{17}$ and $R^{18}$ are independently selected from the group consisting of hydrogen, $C_{1-6}$ alkyl, $C_{3-7}$ cycloalkyl, $C_{2-6}$ alkenyl, $C_{2-6}$ alkynyl, $C_{6-10}$ aryl, $C_{6-10}$ ar($C_{1-4}$)alkyl, pyridyl, pyridyl($C_{1-4}$)alkyl, carboxy($C_{1-6}$)alkyl, $C_{1-4}$ alkoxycarbonyl-($C_{1-4}$)alkyl, cyano($C_{2-6}$)alkyl, hydroxy($C_{2-6}$)alkyl, $C_{1-4}$ alkoxy($C_{2-6}$)alkyl, and mono- and di-($C_{1-4}$)alkylamino($C_{2-6}$)alkyl, or $R^{17}$ and $R^{18}$ can be taken together with the nitrogen atom to which they are attached to form a heterocyclic ring selected from the group consisting of N-morpholino, N-piperazinyl (optionally N' substituted with $C_{1-6}$ alkyl, $C_{1-6}$ hydroxyalkyl, $C_{6-10}$ aryl, $C_{6-10}$ aryl($C_{1-6}$)alkyl, $C_{1-6}$ alkylsulfonyl, $C_{6-10}$ arylsulfonyl, $C_{1-6}$ alkylcarbonyl, morpholino or $C_{6-10}$ arylcarbonyl), N-pyrrolyl, N-piperidinyl, N-pyrrolidinyl, N-dihydropyridyl, and N-indolyl, wherein said heterocyclic ring can be optionally C-substituted;

$R^{23}$, $R^{24}$, $R^{25}$ and $R^{26}$ are each independently one of hydrogen, alkyl, cycloalkyl, alkenyl, alkynyl, optionally substituted aryl, optionally substituted aralkyl, optionally substituted heteroaryl, trifluoromethyl, halogen, hydroxyalkyl, cyano, nitro, carboxamido, —$CO_2R^x$, —$CH_2OR^x$ or —$OR^x$, or when present on adjacent carbon atoms, $R^{23}$ and $R^{24}$ may also be taken together to form one of —CH=CH—CH=CH— or —$(CH_2)_q$—, where q is from 2 to 6, and $R^{25}$ and $R^{26}$ are defined as above;

$R^x$, in each instance, is independently one of hydrogen, alkyl or cycloalkyl wherein said alkyl or cycloalkyl groups may optionally have one or more unsaturations;

Y is one of —O—, —$NR^{19}$—, —S—, —$CHR^{19}$— or a covalent bond;

$R^{19}$, in each instance, is independently hydrogen, $C_{1-6}$ alkyl, benzyl, phenyl, $C_{2-10}$ hydroxyalkyl, $C_{2-10}$ aminoalkyl, $C_{1-4}$ monoalkylamino($C_{2-8}$)alkyl, $C_{1-4}$ dialkylamino($C_{2-8}$)alkyl or $C_{2-10}$ carboxyalkyl;

A is one of

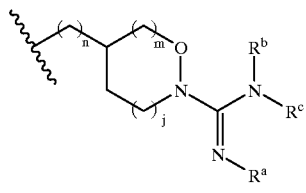

and

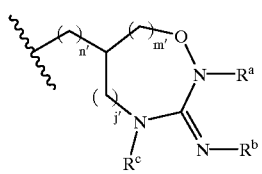

wherein:

$R^a$, $R^b$ and $R^c$ are independently hydrogen, alkyl, hydroxy, alkoxy, aryloxy, aralkoxy, alkoxycarbonyloxy, cyano or —$CO_2R^w$, where
$R^w$ is alkyl, cycloalkyl, phenyl, benzyl,

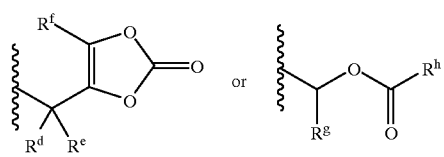

where $R^d$ and $R^e$ are independently hydrogen, $C_{1-6}$ alkyl, $C_{2-6}$ alkenyl or phenyl, $R^f$ is hydrogen, $C_{1-6}$ alkyl, $C_{2-6}$ alkenyl or phenyl, $R^g$ is hydrogen, $C_{1-6}$ alkyl, $C_{2-6}$ alkenyl or phenyl, and $R^h$ is aralkyl or $C_{1-6}$ alkyl;

n and n' are each from zero to 4;
m is from zero to 2;
m' is zero or 1; and
j and j' are each from zero to 2;
provided that n, n', m, m', j and j' are not all zero.

26. A compound of claim 25, having the formula IIa:

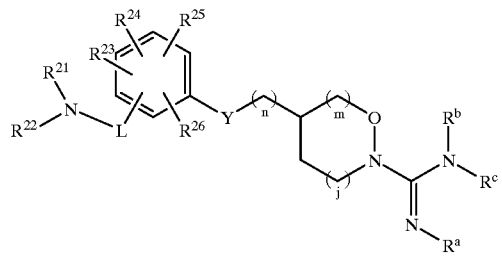

or a solvate, hydrate or pharmaceutically acceptable salt thereof, wherein L, $R^{21}$, $R^{22}$, $R^{23}$, $R^{24}$, $R^{25}$, $R^{26}$, Y, $R^a$, $R^b$, $R^c$, n, m, and j are as defined in claim 25.

27. A compound of claim 25 having the formula IIb:

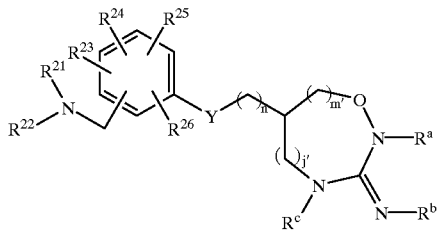

or a solvate, hydrate or pharmaceutically acceptable salt thereof, wherein L, $R^{21}$, $R^{22}$, $R^{23}$, $R^{24}$, $R^{25}$, $R^{26}$, Y, $R^a$, $R^b$, $R^c$, n', m', and j' are as defined in claim 25.

28. A compound of claim 25, wherein:

Q' in $R^{22}$ is $C_{3-6}$ alkenyl or $C_{1-6}$ alkyl, which optionally contains an oxygen group within the chain and is optionally substituted by a group selected from hydroxy, $C_{1-6}$ alkoxy, $NHSO_2R^{16}$, $CO_2R^{15}$, $CONR^{13}R^{14}$, or $SO_2NR^{17}R^{18}$, $R^{12'}$ is hydrogen, $C_{3-7}$ heterocycloalkyl, aryl optionally substituted by $CO_2R^{15}$, heteroaryl optionally substituted by hydroxy, triazole, or tetrazole optionally substituted by $C_{1-6}$ alkyl; and $R^{13}$, $R^{14}$, $R^{15}$, $R^{16}$, $R^{17}$, and $R^{18}$ are as defined in claim 25.

29. A compound of claim 25, wherein:

Q in $R^{21}$ is a bond or $C_{1-6}$ alkyl group, and $R^{12}$ is hydrogen, $C_{3-7}$ cycloalkyl, aryl, or heteroaryl.

30. A compound of claim 29, wherein Q is a bond, and $R^{12}$ is optionally substituted phenyl or $C_{3-7}$ cycloalkyl.

31. A compound of claim 29, wherein Q is $C_{1-4}$ alkyl and $R^{12}$ is hydrogen, cycloalkyl, or heteroaryl.

32. A compound of claim 25, wherein $R^{21}$ and $R^{22}$ are taken together with the nitrogen to which they are attached to form a $C_{3-7}$ heterocycloalkyl or $C_{3-7}$ heterocycloalkenyl group, optionally benzo fused and optionally including an oxygen atom or an additional nitrogen atom, and which may be optionally substituted by $C_{1-6}$ alkyl, hydroxy, $C_{1-4}$ alkoxy, $C_{2-6}$ alkoxycarbonyl, formyl, $(C_{6-10})$ar$(C_{1-4})$alkyl, $C_{6-10}$ aryl, pyridyl, hydroxyalkoxyalkyl, halogen, or $NR^{13}R^{14}$, where $R^{13}$ and $R^{14}$ are as defined in claim 25.

33. A compound of claim 25, wherein $R^{21}$ is $C_{3-7}$ cycloalkyl or $C_{3-7}$ cycloalkenyl, either of which is optionally substituted by $C_{1-6}$ alkyl, hydroxy, $C_{1-4}$ alkoxy, halogen, carboxylic acid, a $C_{1-4}$ carboxylic acid ester group, or $NR^{13}R^{14}$; and $R^{22}$ is $C_{3-6}$ alkenyl, or $C_{3-6}$ alkynyl, either of which is optionally substituted by $C_{1-6}$ alkyl, hydroxy, $C_{1-4}$ alkoxy, halogen, carboxylic acid, a $C_{1-4}$ carboxylic acid ester group, or $NR^{13}R^{14}$;

where $R^{13}$ and $R^{14}$ are as defined in claim 25.

34. A compound of claim 25, wherein:

$R^{21}$ is $C_{3-7}$ heterocycloalkyl($C_{1-6}$)alkyl, $C_{3-7}$ heterocycloalkenyl-($C_{1-6}$)alkyl, heteroaryl($C_{1-6}$)alkyl, $C_{3-7}$ heterocycloalkyl($C_{3-6}$)alkenyl, $C_{3-7}$ heterocycloalkenyl($C_{3-6}$)alkenyl, heteroaryl($C_{3-6}$) alkenyl, $C_{3-7}$ heterocycloalkyl($C_{3-6}$)alkynyl, $C_{3-7}$ heterocycloalkenyl($C_{3-6}$)alkynyl, heteroaryl($C_{3-6}$) alkynyl, di($C_{5-10}$ aryl)($C_{1-3}$)alkyl, di($C_{3-8}$ cycloalkyl) ($C_{1-3}$)alkyl or di($C_{3-8}$ cycloalkenyl)($C_{1-3}$)alkyl, any of which is optionally substituted by $C_{1-6}$ alkyl, hydroxy, $C_{1-4}$ alkoxy, halogen, carboxylic acid, a $C_{1-4}$ carboxylic acid ester group, or $NR^{13}R^{14}$; and $R^{22}$ is as defined in claim 25.

35. A compound of claim 25, wherein $R^{23}$ is hydrogen, $C_{1-3}$ alkyl, halogen, or $C_{1-2}$ alkoxy.

36. A compound of claim 25, wherein $R^{24}$, $R^{25}$, and $R^{26}$ are independently hydrogen or halogen.

37. A compound of claim 25, wherein Y is —O—, $NR^{19}$— or a covalent bond.

38. A compound of claim 1, which is:

3-[(2-amidino(1,2-oxazaperhydroin-5-yl))methoxy]-5-methylphenyl 2-(methylsulfonyl)benzenesulfonate;

3-[(2-amidino(1,2-oxazaperhydroin-5-yl))methoxy]-5-chlorophenyl 2-(methylsulfonyl)benzenesulfonate;

3-[(2-amidino(1,2-oxazaperhydroin-5-yl))methoxy]-5-methylphenyl 2-(methoxy)benzenesulfonate;

3-[(2-amidino(1,2-oxazaperhydroin-5-yl))methoxy]-5-methylphenyl quinolinyl-8-sulfonate;

3-[(2-amidino(1,2-oxazaperhydroin-5-yl))methoxy]-5-methylphenyl 5-chloro-2-(methoxy)benzenesulfonate;

3-[(2-amidino(1,2-oxazaperhydroin-5-yl))methoxy]-5-methylphenyl 5-chlorothiophenyl-2-sulfonate;

3-[(2-amidino(1,2-oxazaperhydroin-5-yl))methoxy]-5-methylphenyl 2-cyanobenzenesulfonate;

3-[(2-amidino(1,2-oxazaperhydroin-5-yl))methoxy]-5-methylphenyl 2-(methylsulfonyl)benzenesulfonate;

3-[(2-amidino(1,2-oxazaperhydroin-5-yl))methoxy]-5-methylphenyl 2-(morpholinylsulfonyl) benzenesulfonate;

3-[(2-amidino(1,2-oxazaperhydroin-5-yl))methoxy]-5-methylphenyl 2-(N-methylphenethylaminosulfonyl) benzenesulfonate;

3-[(2-amidino(1,2-oxazaperhydroin-5-yl))methoxy]-5-methylphenyl 2-[(4-ethyloxycarbonyl) piperidinylsulfonyl]benzenesulfonate;

3-[(2-amidino(1,2-oxazaperhydroin-5-yl))methoxy]-5-methylphenyl 3-[(2,4-bis(methylsulfonyl)] benzenesulfonate;

3-[(2-amidino(1,2-oxazaperhydroin-5-yl))methoxy]-5-methylphenyl 6-[(2,3-dihydro-1,1-dioxobenzo[b] thiophene)]benzenesulfonate;

3-[(2-amidino(1,2-oxazaperhydroin-5-yl))methoxy]-5-methylphenyl 2-[(4-biphenylmethoxy)] benzenesulfonate;

3-[(2-amidino(1,2-oxazaperhydroin-5-yl))methoxy]-5-methylphenyl N-ethyl-3,4-[(methylenedioxy) anilinosulfonyl]benzenesulfonate;

3-[(2-amidino(1,2-oxazaperhydroin-5-yl))methoxy]-5-methylphenyl 3-ethoxycarbonyl-1-(piperidinosulfonyl) benzenesulfonate;

3-[(2-amidino(1,2-oxazaperhydroin-5-yl))methoxy]-5-methylphenyl 2-methoxycarbonyl-1-pyrrolidinosulfonyl-benzenesulfonate;

3-[(2-amidino(1,2-oxazaperhydroin-5-yl))methoxy]-5-methylphenyl 2-(N-propyl-N-(2-(2-pyridyl)ethyl) aminosulfonyl)benzenesulfonate;

3-[(2-amidino(1,2-oxazaperhydroin-5-yl))methoxy]-5-methylphenyl 2-(N,N-bis-(2-cyanoethyl) aminosulfonyl)benzenesulfonate;

3-[(2-amidino(1,2-oxazaperhydroin-5-yl))methoxy]-5-methylphenyl 2-(N-(2-carboxyethyl)-N-benzylaminosulfonyl)benzenesulfonate;

3-[(2-amidino(1,2-oxazaperhydroin-5-yl))methoxy]-5-methylphenyl 2-(4-(carboxymethyl)piperazin-N-1-ylsulfonyl)benzenesulfonate;

3-[(2-amidino(1,2-oxazaperhydroin-5-yl))methoxy]-5-methylphenyl 2-(N-(2-cyanoethyl)-N-(2-furanylmethyl)aminosulfonyl)benzenesulfonate;

3-[(2-amidino(1,2-oxazaperhydroin-5-yl))methoxy]-5-methylphenyl 2-(N-ethyl-N-(1-benzyl-3-pyrrolidinyl) aminosulfonyl)benzenesulfonate; or a pharmaceutically acceptable salt thereof.

39. A compound of claim 25, which is:

5-{[5-chloro-3-(N-cyclopentyl-N-prop-2-enylcarbamoyl) phenoxy]methyl}1,2-oxazaperhydroine-2-carboxamidine;

5-{[5-chloro-3-(4-benzylpiperidinylcarbonyl)phenoxy] methyl}-1,2-oxazaperhydroine-2-carboxamidine;

5-{[5-chloro-3-(N,N-bis [2-methoxyethyl] aminocarbonyl)-phenoxy]methyl}-1,2-oxazaperhydroine-2-carboxamidine;

5-{[5-chloro-3-(N-methyl-N-[3-pyridylmethyl]-aminocarbonyl)phenoxy]methyl}-1,2-oxazaperhydroine-2-carboxamidine;

5-{[5-chloro-3-(N-[2-{dimethylamino}ethyl]-N-ethylaminocarbonyl)phenoxy]methyl}-1,2-oxazaperhydroine-2-carboxamidine;

5-{[5-chloro-3-(4-formylpiperazinylcarbonyl)phenoxy] methyl}-1,2-oxazaperhydroine-2-carboxamidine;

5-{[5-chloro-3-(4-benzylpiperazinylcarbonyl)phenoxy] methyl}-1,2-oxazaperhydroine-2-carboxamidine;

5-{[5-chloro-3-(2-[1,2,3,4-tetrahydro]-isoquinolinylcarbonyl)-phenoxy]methyl}-1,2-oxazaperhydroine-2-carboxamidine;

5-{[5-chloro-3-(azaperhydroepinylcarbonyl)phenoxy] methyl}-1,2-oxazaperhydroine-2-carboxamidine; or a pharmaceutically acceptable salt thereof.

40. A compound of claim 38, which is 3-[(2-amidino(1, 2-oxazaperhydroin-5-yl))methoxy]-5-methylphenyl 2-(methylsulfonyl)benzenesulfonate trifluoroacetate or 3-[(2-amidino(1,2-oxazaperhydroin-5-yl))methoxy]-5-chlorophenyl 2-(methylsulfonyl)benzenesulfonate trifluoroacetate.

41. A compound of claim 39, which is 5-{[5-chloro-3-(N-cyclopentyl-N-prop-2-enylcarbamoyl)phenoxy] methyl}-1,2-oxazaperhydroine-2-carboxamidine trifluoroacetate.

42. A pharmaceutical composition comprising an effective amount of a compound of claim 1 or claim 25 and a pharmaceutically acceptable carrier or diluent.

43. The pharmaceutical composition of claim 42, comprising an 0.01 to 10 mg per kg per day of said compound.

44. A method of inhibiting a trypsin-like protease in a mammal, comprising administering to the mammal a composition of claim 42.

45. The method of claim 44, wherein the trypsin-like protease is chymotrypsin, trypsin, thrombin, plasmin or factor Xa.

46. A method of treating thrombosis, ischemia, stroke, or restenosis, in a mammal, comprising administering to the mammal a composition of claim 42.

47. A method of inhibiting thrombin-induced platelet aggregation and clotting of fibrinogen in plasma, comprising administering to the mammal a composition of claim 42.

48. A method for inhibiting thrombin in blood comprising adding to the blood a compound of claim 1 or claim 25.

49. A method for inhibiting formation of blood platelet aggregates in blood comprising adding to the blood a compound of claim 1 or claim 25.

50. A method for inhibiting thrombus formation in blood comprising adding to the blood a compound of claim 1 or claim 25.

* * * * *

UNITED STATES PATENT AND TRADEMARK OFFICE
CERTIFICATE OF CORRECTION

PATENT NO. : 6,635,637 B2
DATED : October 21, 2003
INVENTOR(S) : Aihua Wang et al.

It is certified that error appears in the above-identified patent and that said Letters Patent is hereby corrected as shown below:

Title page,
Item [73], Assignee, delete "Dimensional Pharmaceuticals, Inc.," and insert
-- 3-Dimensional Pharmaceuticals, Inc., --;
Item [56], References Cited, U.S. PATENT DOCUMENTS, delete "3,271,446 A" and insert -- 3,271,448 A --; also delete "4,764,604 A" and insert -- 4,764,604 B1 --;

Column 2,
Line 26, delete "aprothombinase" and insert -- a prothombinase --;

Column 13,
Lines 16-17, in the compound, delete "$R^c$" and insert -- $R^e$ --;
Line 38, delete "alkyl" and insert -- allyl --;

Column 15,
Line 53, delete "[2-m dimethylamino" and insert -- 2-{dimethylamino} --;

Column 20,
Line 64, delete "$SO_2$" and insert -- $SO_2O$ --;

Column 21,
Line 30, delete "1-carboxamdine" and insert -- 1-carboxamidine --;
Line 55, Scheme III, compound 15, delete "$P^c$" and insert -- $P^e$ --;

Column 22,
Line 45, delete "step" and insert -- steps --;

Column 30,
Line 10, delete "$C_{19}H_{23}NO7S_2$" and insert -- $C_{19}H_{23}NO_7S_2$ --;

Column 34,
Lines 21-22, delete N-N-benzoyl-Phe-Val-Arg-p-nitroanilide" and insert
-- N-benzoyl-Phe-Val-Arg-p-nitroanilide --;

Column 37,
Line 67, delete "$C_{1-4}$" and insert -- $C_{6-14}$ --;

UNITED STATES PATENT AND TRADEMARK OFFICE
CERTIFICATE OF CORRECTION

PATENT NO. : 6,635,637 B2
DATED : October 21, 2003
INVENTOR(S) : Aihua Wang et al.

It is certified that error appears in the above-identified patent and that said Letters Patent is hereby corrected as shown below:

Column 39,
Line 13, after "or" and insert -- $C_{6-10}$ --;

Column 40,
Line 46, delete "consiting" and insert -- consisting --;

Column 41,
Line 42, in the compound delete "$R^c$" and insert -- $R^e$ --;
Line 66, delete "mono alkylaminoalkyl" and insert -- monoalkylaminoalkyl --;

Column 43,
Line 54, delete "$R^c$" and insert -- $R^e$ --;

Column 46,
Line 64, delete "an".

Signed and Sealed this

Twenty-third Day of March, 2004

JON W. DUDAS
*Acting Director of the United States Patent and Trademark Office*